(12) United States Patent
Kim et al.

(10) Patent No.: US 12,257,217 B2
(45) Date of Patent: *Mar. 25, 2025

(54) COMPOSITIONS AND METHODS FOR TREATING HYPERPHAGIA IN PRADER-WILLI SYNDROME

(71) Applicant: Purdue Research Foundation, West Lafayette, IN (US)

(72) Inventors: Kee-Hong Kim, West Lafayette, IN (US); Yuyan Zhu, Shenzhen (CN)

(73) Assignee: Purdue Research Foundation, West Lafayette, IN (US)

( * ) Notice: Subject to any disclaimer, the term of this patent is extended or adjusted under 35 U.S.C. 154(b) by 321 days.

This patent is subject to a terminal disclaimer.

(21) Appl. No.: 18/046,919

(22) Filed: Oct. 15, 2022

(65) Prior Publication Data

US 2023/0270702 A1    Aug. 31, 2023

Related U.S. Application Data

(63) Continuation of application No. 17/343,589, filed on Jun. 9, 2021, now Pat. No. 11,872,198, which is a
(Continued)

(51) Int. Cl.
*A61K 31/18* (2006.01)
*A61K 31/167* (2006.01)
(Continued)

(52) U.S. Cl.
CPC ............ *A61K 31/18* (2013.01); *A61K 31/167* (2013.01); *A61P 3/04* (2018.01); *A61P 3/10* (2018.01);
(Continued)

(58) Field of Classification Search
CPC .. A61K 2300/00; A61K 31/167; A61K 31/18; A61K 45/06; A61P 3/04; A61P 3/06; A61P 3/10; C12N 15/1137; C12N 2310/14; C12N 2310/531; C12N 9/1029; C12Y 203/01009

See application file for complete search history.

(56) References Cited

U.S. PATENT DOCUMENTS 9,168,269 B2    10/2015    Koyuncu et al.
9,206,425 B2    12/2015    Chang et al.

FOREIGN PATENT DOCUMENTS

CN    1414848 A    4/2003
WO    2003/088962 A1    10/2003
(Continued)

OTHER PUBLICATIONS

Ley et al., "RNAi screen in apoptotic cancer cell-stimulated human macrophages reveals co-regulation of IL-6/IL-10 expression," Immunobiology, Feb. 2, 2012, vol. 218, Issue 1, pp. 40-51, ISSN 0171-2985.

(Continued)

*Primary Examiner* — Savitha M Rao
(74) *Attorney, Agent, or Firm* — United One Law Group LLC; Kongsik Kim; Jhongwoo Peck

(57) ABSTRACT

A composition comprising an active agent that inhibits acyl-coenzyme A:cholesterol acyltransferase (ACAT) is provided. With the composition, food intake can be suppressed, and/or body weight can be reduced, and/or metabolic disorders can be prevented and/or treated.

18 Claims, 40 Drawing Sheets

Specification includes a Sequence Listing.

Related U.S. Application Data continuation of application No. 16/461,597, filed as application No. PCT/US2017/061893 on Nov. 16, 2017, now Pat. No. 11,065,216.

(60) Provisional application No. 62/422,722, filed on Nov. 16, 2016.

(51) Int. Cl.
  *A61P 3/04* (2006.01)
  *A61P 3/06* (2006.01)
  *A61P 3/10* (2006.01)
  *C12N 15/113* (2010.01)

(52) U.S. Cl.
  CPC ............ *C12N 15/1137* (2013.01); *A61P 3/06* (2018.01); *C12N 2310/14* (2013.01); *C12N 2310/531* (2013.01)

(56) References Cited

FOREIGN PATENT DOCUMENTS

| | | |
|---|---|---|
| WO | 2011/161964 A1 | 12/2011 |
| WO | 2015/065595 A1 | 5/2015 |

OTHER PUBLICATIONS

Li, J. et al., "Abrogating cholesterol esterification suppresses growth and metastasis of pancreatic cancer," Oncogene, May 2, 2016, vol. 35, Issue 50, pp. 6378-6388, Nature.

Zhu, Y. et al., "Role of Acyl-Coenzyme A: Cholesterol Acyltransferase 1 in Lipogenesis in Adipocytes," Nutrition, Apr. 1, 2015, vol. 29, No. 1, Abstract No. 248.7, The FASEB Journal.

Krause et al., "In vivo evidence that the lipid-regulating activity of the ACAT inhibitor CI-976 in rats is due to inhibition of both intestinal and liver ACAT," Journal of Lipid Research, Feb. 1993, vol. 34, Issue 2, pp. 279-294, American Society for Biochemistry and Molecular Biology.

Llaverias et al., "Pharmacology of the ACAT inhibitor avasimibe (CI-1011)," Cardiovascular Drug Reviews, Feb. 2003, vol. 21, Issue 1, pp. 33-50, Neva Press, Branford, Connecticut.

Pi-Sunyer et al., "Effect of rimonabant, a cannabinoid-1 receptor blocker, on weight and cardiometabolic risk factors in overweight or obese patients: RIO-North America: a randomized controlled trial," JAMA, Feb. 15, 2006, vol. 295, Issue 7, pp. 761-775, JAMA Network.

Netherland et al., "Rimonabant is a dual inhibitor of acyl CoA:cholesterol acyltransferases 1 and 2," Biochemical and Biophysical Research Communications, Aug. 6, 2010, vol. 398, Issue 4, pp. 671-676, ISSN 0006-291X, ScienceDirect.

Proteins Influenced by Avasimibe Treatment in Adipocytes

- downregulated by avasimibe
- upregulated by avasimibe
- little change

Two tail t-test, p<=0.05

FIG. 25

| category | Term | protein Count | category | Term | protein Count |
|---|---|---|---|---|---|
| | actin filament-based process | 5 | | establishment of protein localization | 7 |
| | actin cytoskeleton organization | 4 | | protein localization | 7 |
| | cytoskeleton organization | 5 | | protein transport | 6 |
| | actin filament organization | 3 | | cellular protein localization | 3 |
| | actin cytoskeleton reorganization | 2 | | M phase | 4 |
| | negative regulation of microtubule polymerization or depolymerization | | | cell cycle phase | 4 |
| | | | | cell cycle process | 4 |
| | microtubule-based process | 3 | | cell cycle | 4 |
| | regulation of microtubule polymerization or depolymerization | | | cell division | 3 |
| | | | | striated muscle cell differentiation | 3 |
| | spindle organization | 2 | | muscle cell differentiation | 3 |
| | regulation of microtubule cytoskeleton organization | 2 | | muscle cell development | 2 |
| | regulation of microtubule-based process | 2 | | striated muscle cell development | 2 |
| | negative regulation of cytoskeleton organization | 2 | | cellular macromolecular complex assembly | 3 |
| | cellular protein complex assembly | 3 | | cellular macromolecule localization | 3 |
| | protein complex assembly | 3 | | cellular macromolecular complex subunit organization | |
| | protein complex biogenesis | 3 | | |  |
| | protein polymerization | 2 | | macromolecular complex subunit organization | 3 |
| | negative regulation of protein metabolic process | 2 | | macromolecular complex assembly | 3 |
| | vasculature development | 3 | | intracellular transport | 4 |
| | blood vessel development | 3 | | negative regulation of organelle organization | 2 |

FIG. 26

| category | Term | protein Count | category | Term | protein Count |
|---|---|---|---|---|---|
| redox | oxidation reduction | 22 | nucleotide | purine ribonucleoside triphosphate metabolic process | 5 |
| | cell redox homeostasis | 3 | | nitrogen compound biosynthetic process | 5 |
| TCA | pyruvate metabolic process | 2 | | ribonucleoside triphosphate biosynthetic process | 5 |
| | tricarboxylic acid cycle | 7 | | nucleoside triphosphate biosynthetic process | 5 |
| | acetyl-CoA catabolic process | 7 | | ribonucleoside triphosphate metabolic process | 5 |
| | aerobic respiration | 7 | | purine nucleoside triphosphate metabolic process | 5 |
| | acyl-CoA metabolic process | 2 | | purine ribonucleotide biosynthetic process | 5 |
| | acetyl-CoA metabolic process | 7 | | purine ribonucleotide metabolic process | 5 |
| lipid | fatty acid metabolic process | 11 | | ribonucleotide biosynthetic process | 5 |
| | lipid catabolic process | 4 | | nucleoside triphosphate metabolic process | 5 |
| | lipid modification | 3 | | ribonucleotide metabolic process | 5 |
| | fatty acid oxidation | 3 | | purine nucleotide metabolic process | 5 |
| | lipid oxidation | 3 | | nucleotide biosynthetic process | 5 |
| | cellular lipid catabolic process | 4 | | purine nucleotide biosynthetic process | 5 |
| | fatty acid beta-oxidation | 3 | | nucleobase, nucleoside and nucleotide biosynthetic process | 5 |
| | fatty acid catabolic process | 3 | | | |
| response to hormone stimulation | response to glucocorticoid stimulus | 2 | | nucleobase, nucleoside, nucleotide and nucleic acid biosynthetic process | 5 |
| | response to corticosteroid stimulus | 2 | | | |
| ATP | ATP biosynthetic process | 5 | co-enzyme metabolism | coenzyme catabolic process | 7 |
| | ATP metabolic process | 5 | | coenzyme metabolic process | 10 |

| category | Term | protein Count | category | Term | protein Count |
|---|---|---|---|---|---|
| respiration | cellular respiration | 8 | AA protein | branched chain family amino acid metabolic process | 2 |
| | electron transport chain | 7 | | purine ribonucleoside triphosphate biosynthetic process | 5 |
| | ATP synthesis coupled proton transport | 5 | | purine nucleoside triphosphate biosynthetic process | 5 |
| | energy coupled proton transport, down electrochemical gradient | 5 | membrane transport | transmembrane transport | 7 |
| | | | | monovalent inorganic cation transport | 5 |
| | proton transport | 5 | | ion transmembrane transport | 5 |
| | hydrogen transport | 5 | differentiation | brown fat cell differentiation | 2 |
| carbohydrates | hexose catabolic process | 3 | organic compound metabolism | dicarboxylic acid metabolic process | 3 |
| | glucose catabolic process | 3 | | organic acid catabolic process | 4 |
| | monosaccharide catabolic process | 3 | | energy derivation by oxidation of organic compounds | 8 |
| | gluconeogenesis | 2 | | response to organic substance | 5 |
| | hexose biosynthetic process | 2 | non-organic compound metablism | alcohol catabolic process | 4 |
| | hexose metabolic process | 6 | | hydrogen peroxide metabolic process | 2 |
| | glucose metabolic process | 6 | others | phosphate metabolic process | 7 |
| | monosaccharide metabolic process | 6 | | phosphorus metabolic process | 7 |
| | cellular carbohydrate catabolic process | 4 | | oxidative phosphorylation | 6 |
| | carbohydrate catabolic process | 4 | | homeostatic process | 6 |
| cofactor | cofactor catabolic process | 7 | | carboxylic acid catabolic process | 4 |
| | cofactor metabolic process | 10 | | generation of precursor metabolites and energy | 19 |

COMPOSITIONS AND METHODS FOR TREATING HYPERPHAGIA IN PRADER-WILLI SYNDROME

CROSS REFERENCE TO RELATED APPLICATIONS

This application is a continuation application of U.S. application Ser. No. 17/343,589 filed on Jun. 9, 2021, which is a continuation application of U.S. application Ser. No. 16/461,597 filed on May 16, 2019, which is a U.S. national stage entry of International Application No. PCT/US17/061893 filed on Nov. 16, 2017, which claims the benefits of U.S. Provisional application 62/422,722, filed on Nov. 16, 2016. The applications are incorporated herein by reference.

REFERENCE TO ELECTRONIC SEQUENCE LISTING

The application contains a Sequence Listing which has been submitted electronically in .XML format and is hereby incorporated by reference in its entirety. Said .XML copy, created on Mar. 24, 2023, is named "PUR-P30001C1C3-US.xml" and is 9,756 bytes in size. The sequence listing contained in this.XML file is part of the specification and is hereby incorporated by reference herein in its entirety.

TECHNICAL FIELD

The present invention relates to methods and compositions for suppressing food intake, suppressing body weight, and treating or preventing metabolic diseases.

BACKGROUND

Obesity is an increasingly prevalent disease that has been shown to contribute to a variety of life-threatening medical conditions. Such medical conditions include cardiovascular diseases and metabolic diseases. Current efforts to treat obesity-related diseases are focused on developing drugs or inhibitors of enzymes, transcription factors, and/or signaling proteins involved in neutral lipid (triglyceride) synthesis. However, given that there is still an increasing prevalence of obesity, especially in the United States, there remains a significant need for the identification of additional drug targets for the development of new, safe and effective anti-obesity drugs.

Hyperplasia and hypertrophy are the two major contributors to fat mass expansion during obesity development. Lipid droplet (LD) formation and enlargement are the characteristics of hyperplasia and hypertrophy, respectively. However, the molecular mechanisms regulating LD development in adipocytes have not been fully elucidated (Farese and Walther 2009).

Adipose tissue is also a cholesterol storage organ, in which the majority of the adipocyte cholesterol is found in LDs as free cholesterol (FC) and cholesterol ester (CE) (Farkas, et al. 1973). Several studies also reported a positive correlation between intracellular cholesterol level and TG content (Farkas, et al. 1973, LeLay, et al. 2001, Kovanen, et al. 1975, Schreibman, et al. 1975). Adipose cholesterol content in adipocytes appears to be associated with human obesity as obese humans are reported to store 33-50% of body cholesterol in adipose tissue, while lean ones have about 25% (Schreibman, et al. 1975). LDs found in adipocytes are composed of a neutral lipid core and a phospholipid monolayer (Thiam, et al. 2013). The neutral lipid core contains mainly TG and DG, with some CE and other lipid soluble compounds. The phospholipid monolayer mainly contains phospholipid, cholesterol and proteins associated with LD function. It is known that more than 2000 proteins are increased or decreased≥2 folds during adipogenesis (Welsh, et al. 2004), including proteins associated with lipid synthesis. It is also known that the cholesterol content increases as LD grows, and restricting the cholesterol content can block the development of LD (Dagher, et al. 2003).

Acyl CoA:cholesterol acyl transferases (ACATs) catalyze the formation of CE from long chain fatty acids and cholesterol in the presence of ATP and coenzyme A (Mukherjee, et al. 1958, Chang, et al. 1988, Zhang, et al. 2003). ACAT1 is ubiquitously expressed in different tissues to maintain cholesterol homeostasis, while ACAT2 is known to be mainly expressed in the liver and intestine for CE supply, respectively (Tomoda, et al. 2007). Both ACAT1 and ACAT2 are considered to be drug targets for the treatments of not only atherosclerosis (Yagyu, et al. 2000, Fazio, et al. 2001) but also cancer (Yue, et al. 2014) and Alzheimer's diseases (Shibuya, et al. 2015, Bhattacharyya, et al. 2010). Moreover, this invention demonstrates that ACATs are required for LD formation and increasing intracellular cholesterol content during adipogenesis in vitro. Therefore, ACAT may play a critical role in the network of LD development. Since cholesterol homeostasis impacts adipocyte function (Yu, et al. 2010), ACAT inhibition may impact various biological processes besides lipogenesis.

Diabetes is the $7^{th}$ leading cause of death affecting more than 10% of adults and 26% of seniors of the U.S. population, largely due to its related health complications, including hypertension, heart attack, stroke, kidney diseases and eye problems. The total cost of diagnosed diabetes in the U.S. is approximately $245 billion and around $176 billion is spent for direct medical costs. Type 2 diabetes (T2D) is characterized by "insulin resistance" as the body doesn't properly handle blood glucose when insulin is present. About 90-95% of all North American cases of diabetes are T2D. T2D and obesity are closely inter-connected as more than 85% of patients with T2D are also obese. Indeed, obesity has been shown to contribute to a variety of life-threatening medical conditions such as T2D and its related health complications.

Currently, approximately 10 of the best-selling anti-diabetes drugs comprise approximately $28.6 billion globally. Many of the available anti-diabetes drugs (e.g., rosiglitazone, pioglitazone, sitagliptin, saxagliptin, liragliptin, exenatide, liraglutide and albiglutide) are associated with an undesirable increase or little effect on adipose mass and weight gain, which compromise the overall efficacy of diabetes therapy as well as the quality of life for the patients. Given the facts that the majority of T2D patients is already overweight and obese, physicians are often recommendation to elect T2D drugs with favorable additional effects on weight loss.

Combined effect of a PPARα/γ dual agonist and ACAT inhibitors on the treatment of hyperglycemia, lipid disorders, and obesity in a patient having T2D was reported (e.g., WO 2003/088962). However, no evidence of direct effects of ACAT inhibitor alone on body weight, food intake and insulin resistance was presented.

Various methods for treating lipid disorders or hyperlipidemia and suppressing obesity by administering ACAT2 inhibitors and ACAT1-selective inhibitors orally or parenterally have been proposed, as disclosed in, e.g., WO 2009/081957, KR1020030011474, U.S. Application Publication No. 2011/0184173, EP2228376, and WO2015065595.

Nowhere, however, do these disclosures indicate that administration of ACAT inhibitors were associated with suppression of food intake and its-related body weight loss and insulin sensitivity.

This BACKGROUND section introduces aspects that may help facilitate a better understanding of the disclosure. Accordingly, it should be read in this light and it should not be understood as admissions about what is or is not prior art. The references cited herein are incorporated herein by reference.

SUMMARY

In one aspect, the present invention provides a composition for suppressing food intake, reducing body weight, and/or preventing/treating metabolic disorders. The composition comprises an effective amount of an active agent that can inhibit acyl-coenzyme A:cholesterol acyltransferase (ACAT).

In some embodiments, the active agent can inhibit ACAT1, ACAT2, or both. In some cases, the degree that the active agent inhibits ACAT1 may be similar to or less than the degree that the active agent inhibits ACAT 2.

In some embodiments, the composition may comprise avasimibe as the active agent. The composition may comprise CI-976 as the active agent. The composition may comprise both avasimibe and CI-976 as the active agents.

In another aspect, the present invention provides a method for suppressing food intake of a subject. The method comprises administering to the subject the above-described composition.

In some embodiments, the effective amount may be in the range of about 0.01 mg/kg/day to about 200 mg/kg/day.

In some embodiments, the composition may be administered parenterally. For example, the composition may be administered subcutaneously, intravenously, or intraperitoneally.

In some embodiments, the method can reduce body weight. The method can prevent or treat metabolic disorders.

In some embodiment, the high fat diet fed subject administered with the active agent has decreased level of free cholesterol, CE and TG compared to a subject having high fat diet without the active agent administration.

In another aspect the present invention provides an shRNA sequence to knockdown ACAT1 comprising SEQ ID NO:5.

In another aspect the present invention provides an shRNA sequence to knockdown ACAT2 comprising SEQ ID NO:6.

In yet another aspect the present invention provides a method of inhibiting synthesis of fatty acids and TGs in adipocytes. The method comprises introducing an shRNA sequence operably integrated to a lentivirus vector to the adipocytes, wherein the shRNA sequence is selected from the group consisting of SEQ ID NO:5 and SEQ ID NO:6.

Each embodiment disclosed herein is contemplated as being applicable to each of the other disclosed embodiments. Thus, all combinations of the various elements described herein are within the scope of the invention. Other aspects are described infra.

BRIEF DESCRIPTION OF THE DRAWINGS

FIG. 25 is a list of biological processes to which proteins upregulated by avasimibe in adipocytes relate.

FIG. 26 and FIG. 27 are lists of biological processes to which proteins downregulated by avasimibe in adipocytes relate.

DETAILED DESCRIPTION OF EXEMPLARY EMBODIMENTS

Figure 1:
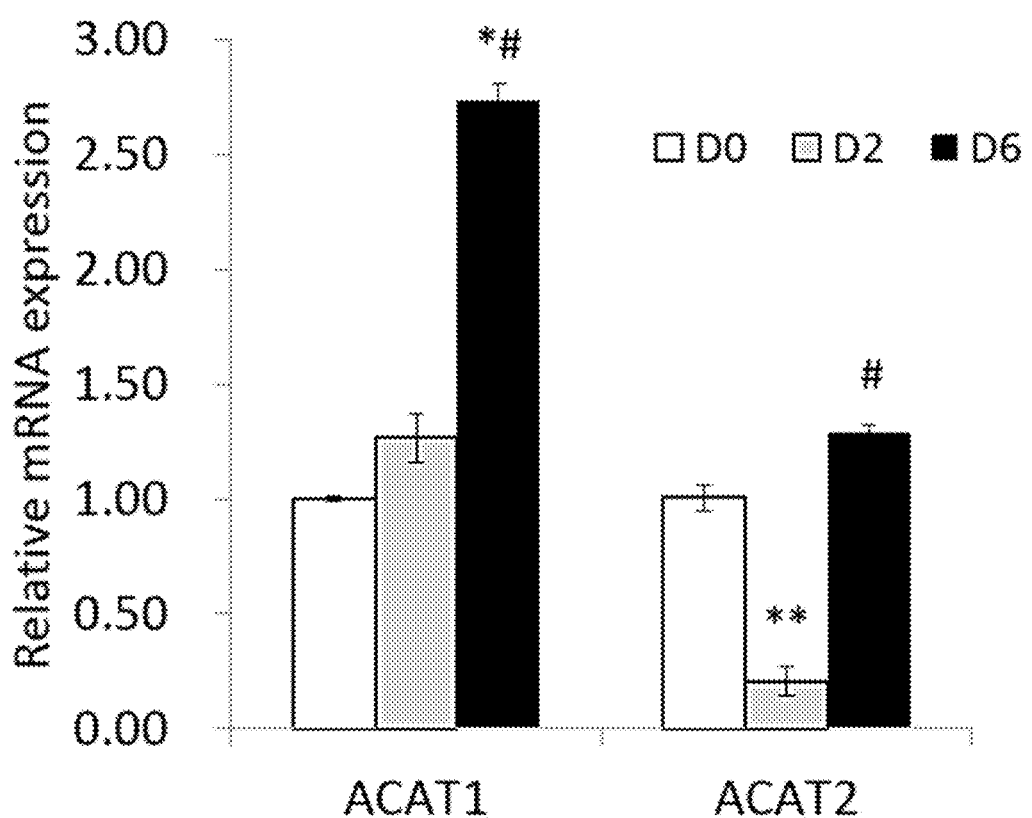
FIG. 1 is a bar graph showing the relative mRNA expression of ACAT1 and ACAT2 in preadipocytes (DO), immature adipocytes (D2) and mature adipocytes (D6).

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Definitions

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The abbreviations used herein have their conventional meaning within the chemical and biological arts. The chemical structures and formulae set forth herein are constructed according to the standard rules of chemical valency known in the chemical arts.

As used herein, the singular forms "a", "an" and "the" are intended to include the plural forms as well, unless the context clearly indicates otherwise. Thus, for example, reference to "a polypeptide" includes mixtures of polypeptides, reference to "a pharmaceutical carrier" includes mixtures of two or more such carriers, and the like.

As defined herein, the terms "about" or "approximately" mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As defined herein, the terms "activation", "activate", "activating" and the like in reference to a protein-activator (e.g. agonist) interaction mean positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a harmful mediator/substance decreased in a disease. Activation may include, at least in part, partially or totally increasing stimulation, increasing or enabling activation, or activating, sensitizing, or up-regulating signal transduction or enzymatic activity or the amount of a harmful mediator/substance.

As defined herein, the term "administering" means oral administration, administration as a suppository, topical contact, intravenous, parenteral, intraperitoneal, intramuscular, intralesional, intrathecal, intracranial, intranasal, intraocular, intracardiac, intravitreal, intracerebral, intraosseous, intraarterial, intraarticular, intradermal, transdermal, transmucosal, sublingual, enteral, sublabial, insufflation, inhaled or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "coadminister" it is meant that a composition described herein is administered at the same time, just prior to, or just after the administration of one or more additional therapies (e.g. anti-obesity agent). The compound can be administered alone or can be coadministered to the patient. Co-administration is meant to include simultaneous or sequential administration of the compound individually or in combination (more than one compound or agent). In some embodiments, a first composition comprising a first ACAT inhibitor (e.g., (e.g., avasimibe) as the active agent and a second composition comprising a second ACAT inhibitor (e.g., CI-976) as the active agent can be co-administered.

The preparations can also be combined, when desired, with other active substances (e.g. to reduce metabolic degradation, to increase degradation of a prodrug and release of the drug, detectable agent). The compositions can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In another embodiment, the formulations of the compositions can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions can also be delivered as nanoparticles.

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense oligonucleotides, siRNA reagents, antibodies, antibody fragments bearing epitope recognition sites, peptoids, aptamers, enzymes, peptides organic or inorganic molecules, natural or synthetic compounds and the like. An agent can be assayed in accordance with the methods of the invention at any stage during clinical trials, during pre-trial testing, or following FDA-approval.

As defined herein, the terms "alter", "altering" "alteration" and the like are meant a change (increase or decrease) in the expression levels or activity of a gene or polypeptide as detected by standard art known methods such as those described herein.

As defined herein, the term "ameliorate" is meant decrease, suppress, attenuate, diminish, arrest, or stabilize the development or progression of a disease.

As defined herein, the terms "associated" or "associated with" in the context of a substance or substance activity or function associated with a disease (e.g. obesity) mean that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with weight gain such as obesity may be treated with an agent (e.g. compound as described herein) effective for decreasing weight gain.

As used herein, the terms "comprising." "comprise" or "comprised," and variations thereof, in reference to defined or described elements of an item, composition, apparatus, method, process, system, etc., are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc. The terms "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. Furthermore, to the extent that the terms "including." "includes," "having," "has," "with," or variants thereof are used in either the detailed description and/or the claims, such terms are intended to be inclusive in a manner similar to the term "comprising."

As defined herein, the terms "control" or "standard control" are used in accordance with its plain ordinary meaning and refers to a sample that serves as a reference, usually a known reference, for comparison to a test sample. For example, a test sample can be taken from a patient suspected of having a given disease (e.g., obesity or diabetes) and compared to samples from a known obesity or diabetes patient, or a known normal (e.g., non-disease) individual. A control can also represent an average value gathered from a population of similar individuals, e.g., obesity or diabetes patients or healthy individuals with a similar medical background, same age, weight, etc. A control can also be obtained from the same individual, e.g., from an earlier-obtained sample, prior to disease, or prior to treatment. One of skill will recognize that controls can be designed for assessment of any number of parameters, and one of skill will understand which controls are valuable in a given situation and be able to analyze data based on comparisons to control values. Controls are also valuable for determining the significance of data. For example, if values for a given parameter are widely variant in controls, variation in test samples will not be considered as significant.

As defined herein, the terms "disease" or "condition" refer to a state of being or health status of a patient or subject capable of being treated with a compound, pharmaceutical composition, or method provided herein. In some embodiments, the disease is a disease having an increase in body weight. In some embodiments, the disease is obesity. Obesity may be the primary cause of the disease and/or disease to be treated or may also by a result of the primary disease and/or disorder. In some embodiments, the disease is a metabolic disease, such as diabetes.

The terms "metabolic disease." "metabolic disorder" and "metabolic syndrome" are used interchangeably to refer to any condition in which there is a defect of metabolism, typically due to a genetic defect. Non-limiting examples of metabolic processes that can be impacted include carbohydrate, protein, and/or fat metabolic pathways in food to release energy, transformation of excess nitrogen into waste products excreted in urine and the breaking down or converting chemicals into other substances and transporting them inside cells.

As used herein, the term "effective amount" refers to an amount sufficient for a compound to accomplish a stated purpose relative to the absence of the compound (e.g. achieve the effect for which it is administered, treat a disease, reduce enzyme activity, increase enzyme activity, reduce signaling pathway, reduce one or more symptoms of a disease or condition). An example of an "effective amount" is an amount sufficient to contribute to the treatment, prevention, or reduction of a symptom or symptoms of a disease, which could also be referred to as a "therapeutically effective amount."

As defined herein, the term "in combination" in the context of the administration of a therapy to a subject refers to the use of more than one therapy (e.g., prophylactic and/or therapeutic). The use of the term "in combination" does not restrict the order in which the therapies, concomitantly with, or subsequent to the administration of a second therapy to a subject which had, has, or is susceptible to obesity or diabetes. In some embodiments, the therapies are administered to a subject in a sequence and within a time interval such that the therapies can act together. In some embodiments, the therapies are administered to a subject in a sequence and within a time interval such that they provide an increased benefit than if they were administered otherwise. Any additional therapy can be administered in any order with the other additional therapy.

As defined herein, the terms "inhibition," "inhibit," "inhibiting," and the like in reference to a protein-inhibitor (e.g. antagonist) interaction mean negatively affecting (e.g. decreasing) the level of activity or function of the protein relative to the level of activity or function of the protein in the absence of the inhibitor. In some embodiments, inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the terms "modulate," "modulating." and the like refer to increasing or decreasing the level of a target molecule or the function of a target molecule.

As used herein, the term "or" is generally employed in its sense including "and/or" unless the content clearly dictates otherwise.

As defined herein, the terms "pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As defined herein, the terms "prevent." "preventing." "prevention," "prophylactic treatment" and the like refer to reducing the probability of developing a disease or condition in a subject, who does not have, but is at risk of or susceptible to developing a disease or condition.

As defined herein, the term "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and it may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As defined herein, the terms "subject", "patient", "individual" and the like refer to a living organism who suffers from or is susceptible to a disease or condition that can be treated by administration of a compound or pharmaceutical composition as provided herein. Non-limiting examples include humans, vertebrates, other mammals, bovines, birds, rats, mice, dogs, cats, horses, primate, fowls, pigs, apes, monkeys, goats, camels, sheep, cows, deer, and other non-mammalian animals. In some embodiments, the subject is a companion animal, such as a dog or a cat. In some embodiments, a patient is human. In some embodiments, the patient is pre-obese, obese or morbidly obese. In some embodiments, the patient is not pre-obese, obese, or morbidly obese, but was formerly pre-obese, obese, or morbidly obese. In some embodiments, the patient wishes to lose weight or have a decreased appetite. Alternatively or in addition, a patient has an obesity-related disease or disorder. These examples are not limiting. The terms "subject." "patient." "individual," and the like as used herein are not intended to be limiting and can be generally interchanged. That is, an individual described as a "patient" does not necessarily have a given disease or is not necessarily under the care of a medical professional, but it may be merely seeking or wish to have treatment in the absence of medical advice (such as self-treatment). In accordance with the methods described herein, a "subject in need of" is a subject with overweight or obesity or related disease or T2D, or a subject having an increased risk of developing overweight or obesity T2D or related disease.

As defined herein, the terms "suppression", "suppress", "suppressing" and the like, or the terms "reduction", "reduce" or "reducing" and the like of a symptom or symptoms (and grammatical equivalents of this phrase) mean decreasing of the severity or frequency of the symptom(s), or elimination of the symptom(s).

As used herein, the terms "therapies" and "therapy" can refer to any protocol(s), method(s), composition(s), formulation(s), and/or agent(s) that can be used in the prevention or treatment of a disease or symptom associated therewith. In certain embodiments, the terms "therapies" and "therapy" refer to biological therapy, supportive therapy, and/or other therapies useful in treatment or prevention of a disease or symptom associated therewith known to one of skill in the art.

As defined herein, the terms "treating" or "treatment" refer to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with weight gain such as obesity.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning. 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, $6^{th}$ Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), ($4^{th}$ Ed., Univ. of Oregon Press, Eugene, 2000).

Obesity

Obesity is characterized by excessive WAT, which is attributed to increased adipocyte number (hyperplasia) and lipid storage (hypertrophy). Adipocyte hyperplasia and hypertrophy are governed by an increase in adipogenesis and LD accumulation, respectively. Therefore, regulating adipogenesis is an effective strategy to control obesity and its associated diseases, such as atherosclerosis and other cardiovascular diseases (CVDs).

The term "obese", as used herein, refers to a patient having a body mass index of greater than 30 kg/m$^2$. "Overweight" and "pre-obese", as used herein, refer to patients having a body mass index of greater than 25 kg/m$^2$. "Morbidly obese", as used herein, refers to a patient having a BMI of greater than 40 mg/m$^2$, a BMI of greater than 35 kg/m$^2$ in combination with one or more co-morbidities, a BMI of greater than 30 kg/m$^2$ in combination with uncontrollable diabetes, or combinations thereof.

The term "obesity-related diseases," as used herein, comprises obesity, pre-obesity, morbid obesity, Prader-Willi Syndrome, Pro-opiomelanocortin (POMC) deficiency obesity, LepR deficiency obesity, POMC heterozygous deficiency obesity, and POMC epigenetic disorders, Alström syndrome, Hypothalamic Injury Associated Obesity, Non-alcoholic steatohepatitis, hyperlipidemia, hypertension, diabetes, lipodystrophy, fatty liver, Bardet-Biedl Syndrome, Cohen Syndrome, cardiovascular disease, arthritis, stroke, metabolic syndrome and MOMO (Macrosomia Obesity Macrocephaly Ocular abnormalities) Syndrome.

The term "anti-obesity agent" refers to the property of a substance or treatment that reduces weight gain and promotes weight loss. Examples of anti-obesity agents would be Sibutramine, Phentermine, Mazindol, Diethylpropion, Leptin, Orlistat, Beta-3 agonists, and Rimonabant.

In one aspect, the present invention provides methods of suppressing food intake of a subject, comprising: administering an effective amount of an agent inhibiting ACAT to the subject. In some embodiments, the agent inhibits ACAT1 and/or ACAT2. In some embodiments, the degree that the active agent inhibits ACAT1 may be similar to or less than the degree that the active agent inhibits ACAT 2. In some embodiments, the agent is selected from the group consisting of an antibody or fragment thereof, polypeptide or fragments thereof, small molecules, and nucleic acids. In some embodiments, the agent comprises ACAT non-selective inhibitors, such as avasimibe or CI-976. In some embodiments, the agent comprises avasimibe, CI-976, or both. In some embodiments, the effective amount of the agent is from about 0.01 mg/kg/day to about 200 mg/kg/day. In some embodiments, the agent is administered parenterally. For example, the agent may be administered subcutaneously, intravenously, or intraperitoneally. In some embodiments, the agent is administered by an intravenous injection. In one aspect, the present invention provides a pharmaceutical composition comprising an agent inhibiting ACAT to suppress food intake of a subject and one or more pharmaceutically acceptable excipient.

Suppressing food intake of a subject according to the methods described herein, preferably result in a reduction of food intake of a subject by at least about 10% or greater relative to the amount, volume, weight and/or calorie of the food intake of the subject prior to treatment; more preferably, a reduction of food intake of a subject by at least about 20% or greater; more preferably, a reduction of food intake of a subject by at least about 30% or greater; more preferably, a reduction of food intake of a subject by at least about 40% or greater; more preferably, a reduction of food intake of a subject by at least about 50% or greater; even more preferably, a reduction of food intake of a subject by at least about 60% or greater; and most preferably, a reduction of food intake of a subject by at least about 70% or greater. The food intake may be assessed by any reproducible means of measurement. The food intake may be measured as an amount, a volume, a weight and/or a caloric.

In one aspect, the present invention provides methods of reducing body weight of a subject, comprising: administering an effective amount of an agent inhibiting ACAT to the subject and thereby suppressing food intake of the subject. In some embodiments, the agent inhibits ACAT1 and/or ACAT2. In some embodiments, the degree that the active agent inhibits ACAT1 may be similar to or less than the degree that the active agent inhibits ACAT 2. In some embodiments, the agent is selected from the group consisting of an antibody or fragment thereof, polypeptide or fragments thereof, small molecules, and nucleic acids. In some embodiments, the agent comprises ACAT non-selective inhibitors, such as avasimibe or CI-976. In some embodiments, the agent comprises avasimibe or CI-976. In some embodiments, the effective amount of the agent is from about 0.01 mg/kg/day to about 200 mg/kg/day. In some embodiments, the agent is administered parenterally. For example, the agent may be administered subcutaneously, intravenously, or intraperitoneally. In some embodiments, the agent is administered by an intravenous injection. In some embodiments, the agent suppresses a lipid accumulation in a body of the subject. In one aspect, the present invention provides a pharmaceutical composition comprising an agent inhibiting ACAT to suppress body weight of a subject and one or more pharmaceutically acceptable excipient.

In some embodiments, reducing body weight of a subject according to the methods described herein refers to suppressing gain of body weight of a subject. Suppressing gain of body weight of the subject preferably results in maintaining body weight of a subject within at most about 110% or lesser relative to the body weight of the subject prior to treatment; more preferably, maintaining body weight of a subject within at most about 109% or lesser; more preferably, maintaining body weight of a subject within at most about 108% or lesser; more preferably, maintaining body weight of a subject within at most about 107% or lesser; more preferably, maintaining body weight of a subject within at most about 106% or lesser; more preferably, maintaining body weight of a subject within at most about 105% or lesser; more preferably, maintaining body weight of a subject within at most about 104% or lesser; more preferably, maintaining body weight of a subject within at most about 103% or lesser; more preferably, maintaining body weight of a subject within at most about 102% or lesser; even more preferably, maintaining body weight of a subject within at most about 101% or lesser; and most preferably, maintaining body weight of a subject within at most about 100%. The body weight may be assessed by any reproducible means of measurement.

In some embodiments, reducing body weight of a subject according to the methods described herein refers to a reduction of body weight of a subject. A reduction of body weight of a subject preferably result in a reduction of body weight of a subject by at least about 5% or greater relative to the body weight of the subject prior to treatment; more preferably, a reduction of body weight of a subject by at least about 10% or greater; more preferably, a reduction of body weight of a subject by at least about 15% or greater; more preferably, a reduction of body weight of a subject by at least about 20% or greater; more preferably, a reduction of body weight of a subject by at least about 25% or greater; more preferably, a reduction of body weight of a subject by at least about 30% or greater; even more preferably, a reduction of body weight of a subject by at least about 35% or greater; and most preferably, a reduction of body weight of a subject by at least about 40% or greater. The body weight may be assessed by any reproducible means of measurement.

In some embodiments, suppression of gaining body weight of a subject according to the methods described herein is attributed to total WAT weight loss. Total WAT weight of the subject is preferably decreased by at least about 5% or greater relative to the total WAT weight of the subject prior to treatment; more preferably, decreased by at least about 10% or greater; more preferably, decreased by at least about 15% or greater; more preferably, decreased by at least about 20% or greater; more preferably, decreased by at least about 25% or greater; more preferably, decreased by at least about 30% or greater; even more preferably, decreased by at least about 35% or greater; and most preferably, decreased by at least about 40% or greater. The total WAT weight may be assessed by any reproducible means of measurement.

Adipogenesis

Adipogenesis is the process of cell differentiation in which preadipocytes become mature adipocytes. There are four distinct stages required for transition from preadipocytes to mature adipocytes: 1) growth arrest; 2) mitotic clonal expansion (additional 2-3 rounds of cell cycle); 3) early differentiation; and 4) intermediate and terminal differentiation. Upon induction of adipogenesis, the growth-arrested 3T3-L1 preadipocytes undergo mitotic clonal expansion with activation/expression of cell cycle proteins, such as cdk2 and cyclinA. Mitotic clonal expansion is also accompanied by activation of cellular signaling pathways, such as insulin-dependent phosphatidylinositol (PI) 3-kinase and extracellular signal-regulated kinase (ERK) pathway, which then initiates the expression of a series of adipogenic transcription factors. The major adipogenic transcription factors orchestrating the adipogenesis are CCAAT/enhancer binding protein (C/EBP)β, C/EBPα and peroxisome proliferator-activated receptorγ (PPARγ). C/EBPβ is expressed in the early stage of differentiation after clonal expansion, which is required for the subsequent expression of C/EBPα and PPARγ. During the termination phase of adipogenesis, differentiating cells markedly increase expression of genes involved in de novo lipogenesis and TG synthesis, including ATP citrate lyase, acetyl-CoA carboxylase (ACC), stearoyl-CoA desaturase 1 (SCD1), glycerol-3-phosphate acyltransferase (GPAT), glycerol-3-phosphate dehydrogenase, fatty acid synthase (FAS), glyceraldehyde-3-phosphate dehydrogenase (GAPDH), monoglyceride acyltransferase (MGAT), and diglyceride acyltransferase (DGAT), resulting in generation of new LDs and expansion of both adipocyte cell number and size. Given that adipocyte number is the major determinant of increase in adipose mass during childhood and adolescence both in lean and obese humans, inhibition of adipogenesis has been suggested to be an effective strategy in lowering the generation and formation of new adipocytes and thereby decreasing or suppressing the overall adipose mass.

Adipogenesis has been reported to be associated with sharp increments in TG, CE and cholesterol in vitro. Additionally, approximately 280-fold increase in cholesterol esterase activity is observed during 3T3-L1 adipogenesis. During adipogenesis, most of the cellular cholesterol and CE in adipocytes reside in the plasma membrane and LDs. These reports indicate a potential role of CE, a storage form of cholesterol, in functional homeostasis of adipocytes.

Lipid Body

LDs, also referred to as lipid bodies, oil bodies or adiposomes, are lipid-rich cellular organelles that regulate the storage and hydrolysis of neutral lipids and are found largely in the adipose tissue. They also serve as a reservoir for cholesterol and acyl-glycerols for membrane formation and maintenance. LDs are found in all eukaryotic organisms and store a large portion of lipids in mammalian adipocytes. Adipose tissue is largely viewed as an energy reservoir in a form of LD.

TGs are a major lipid found in LDs, and cholesterol and CE make up the neutral core of LDs found in adipocytes and macrophages, which are wrapped by a monolayer of phospholipids and other polar lipids. On the other hand, retinol esters are prominent neutral lipids found in LDs in liver stellate cells. The structure of LDs is maintained and stabilized by various LD-binding proteins, such as patatin-like phospholipase domain-containing proteins (e.g., perilipin1, perilipin2/adipophilin (ADRP), perilipin3/Tip47, and perilipin4/S3-12), cell death inducing DNA fragmentation factor proteins (CIDEs), fat-specific protein of 27 kDa (FSP27), and several lipases.

Defects in function of many of these LD-binding proteins have been reported to be associated with impaired adipogenesis and LD generation in adipocytes. LD growth is facilitated by activated endoplasmic reticulum (ER) resident enzymes, such as DGAT for TG synthesis and ACATs for cholesterol ester synthesis. These are also accompanied by activation of de novo lipogenesis and fatty acid/cholesterol uptake in adipocytes. LDs are highly dynamic cellular compartments whose generation of fatty acids in response to an increased diet, and degradation of fatty acids in response to a lack of systemic nutrient availability are tightly controlled to maintain whole body energy and inflammation homeostasis.

Accordingly, alteration of intracellular LD accumulation is associated with a wide range of metabolic and inflammatory human diseases, such as lipodystrophy-associated insulin resistance, hepatic steatosis, and hypertension. Likewise, over-accumulation of TG- and CE-containing LD both in adipose tissue and other non-adipose peripheral tissues, such as the heart, liver and muscle, is also associated with neutral lipid storage disease, cardiomyopathy, obesity, T2D, steatohepatitis, and coronary heart disease.

Because TG is the predominant lipid in LD accumulated in most tissues, current therapies for treating the aforementioned chronic diseases have focused on developing methods to suppress enzymes and genes involved in fatty acid and TG synthesis. In addition to the role of TG in LD biology in adipocytes, adipose tissue is also one of the largest reservoirs of cholesterol and the size of cholesterol pool in adipocytes is proportional to the TG content and LD size. Despite the fact that cholesterol content in adipocytes is known to be controlled by cholesterol synthesis, catabolism efflux and/or influx, little is known about the role of cholesterol metabolism in LD growth and size in adipose tissue, and the development of adiposity.

ACATS/SOATS

Acyl-coenzyme A:cholesterol acyltransferase (ACAT), also known as sterol O-acyltransferase (SOAT), play an important role in cellular cholesterol esterification and thus late intestinal cholesterol absorption and hepatic lipoprotein secretion. ACATs catalyze the formation of CE from long chain fatty acid and cholesterol in the presence of ATP and coenzyme A. The two substrates of this enzyme are acyl-CoA and cholesterol, whereas its two products are CoA and CE. This enzyme belongs to the family of transferases, specifically those of acyltransferases transferring groups other than aminoacyl groups, the membrane-bound O-acyltransferases, and also participates in bile acid biosynthesis.

Both ACAT1 and ACAT2 are located in the endoplasmic reticulum (ER) membrane and are both allosterically activated by cholesterol. While ACAT1 is ubiquitously expressed in various tissues, ACAT2 is mainly expressed in the liver and intestine for supplying CE as the lipid core of very low density lipoprotein and chylomicrons, respectively.

As CE constitutes most LDs in macrophages and has a positive correlation with lipid-laden form cell formation, ACATs have been suggested to be therapeutic targets for atherosclerosis and hypercholesterolemia. Although ACAT2 knockout mice showed prevention against diet-induced hypercholesterolemia by losing the cholesterol esterification activity in intestine and liver, the role of ACAT1 in atherosclerosis is controversial as hyperlipidemic mice with reconstituted ACAT1$^{-/-}$ macrophages presented either detrimental or preventive function in atherosclerosis depending on the study designs.

In addition to the role of ACATs in hypercholesterolemia, CE synthesis appears to play important role in TG synthesis and LD biology. For example, yeast with a lack of TG and sterol ester displayed a defect in LD biogenesis with excess accumulation of neutral lipids in between membrane bilayers. However, the role of CE and ACATs in adipose development and LD biogenesis in adipocytes has not yet been explored.

As mentioned above, obesity is characterized by increased LD due to excess accumulation of lipids in adipose tissue. LD is composed of mostly neutral lipids, such as triglycerides, cholesterol esters, phospholipids and LD-binding proteins. It is herein disclosed that ACAT1 and ACAT2, are key enzymes involved in catalyzing the conversion of free cholesterol to CE, and are accordingly preventive and therapeutic targets for lowering fatty acid synthesis, LD accumulation and the development of obesity. In some embodiments, the use of avasimibe, a commercially available drug developed to control atherosclerosis is used as an inhibitor of ACAT1 and ACAT2, and thereby regulating, treating and/or preventing obesity.

Type-2 Diabetes (T2D)

Compositions and methods for treating T2D with improved blood glucose homeostasis and reduction of body weight have been developed. Excessive white adipose tissue mass contributes to the development of obesity and insulin resistance, which are attributed to increased adipocyte number (hyperplasia) and lipid storage (hypertrophy). Adipocyte hyperplasia and hypertrophy are governed by an increase in adipogenesis and LD accumulation as described above. Therefore, regulating adipogenesis and/or LD generation is one of the effective strategies to control insulin resistance and obesity. As mentioned above, LD is composed of mostly neutral lipids, such as triglycerides, cholesterol esters, phospholipids and LD-binding proteins. It is herein disclosed that ACAT1 and ACAT2, the key enzymes catalyzing conversion of free cholesterol to cholesterol ester, are preventive and therapeutic target for modulating glucose and insulin sensitivity and lowering body fat and food intake.

ACAT Inhibitors

As used herein, an "ACAT inhibitor" is an agent that inhibits ACAT enzymatic activity and/or expression. More specifically, the ACAT inhibitor is selected from the group consisting of an antibody or fragment thereof, peptides, polypeptides or fragments thereof, small molecules, and an inhibitory nucleic acid. The term "ACAT1" and "ACAT2", include variants, isoforms, species homologs of human ACAT1 and ACAT2. The complete ACAT1 amino acid sequence can be found under GENBANK® Accession No. AAH10942.1 (GI: 15012080) and is shown below (SEQ ID NO: 1):

mavlpallrs garsrspllr rlvqeiryve rsyvskptlk evvivsatrt pigsflgsls llpatklgsi aiqgaiekag ipkeevkeay mgnvlqggeg qaptrqavlg aglpistpct tinkvcasgm kaimmasqsl mcghqikqet gslakicchv rr The complete ACAT1 nucleic acid sequence can be found under GENBANK® Accession No. BC010942 (GI: 15012079) and is shown below (SEQ ID NO: 2):

ggggagtcta cgcctgtgga gccgatactc agcccactgc gaccatggct gtgctgccgg cacttctgcg cagcggcgcc cgcagccgca gccccctgct ccggaggctg gtgcaggaaa taagatatgt ggaacggagt tatgtatcaa aacccacttt gaaggaagtg gtcatagtaa gtgctacaag aacacccatt ggatcttttt taggcagcct ttccttgctg ccagccacta agcttggttc cattgcaatt cagggagcca ttgaaaaggc agggattcca aagaagaag tgaaagaagc atacatgggt aatgttctac aaggaggtga aggacaagct cctacaaggc aggcagtatt gggtgcaggc ttacctattt ctactccatg taccaccata aacaaagttt gtgcttcagg aatgaaagcc atcatgatgg cctctcaaag tcttatgtgt ggacatcaga tcaagcaaga gacaggctcc ttagcaaaaa tatgctgtca tgtcaggagg tgagacctgg acacacagaa gaatcaagat tctctcagat ctgagcccct cattttcag atgaagattt tttttcagtg tgtctgagac agccacagag ttacagggct gagcatctgc catgtgacag tcattggaaa tagagtggtg aacaaaacat ttaaaaaaat ctgtacatgt gcaggtctct gttggaaaaa tgcctaaaag aaatgctgag tcaggatttg aacattttgg tatttgcaaa tgctttccat aaaagttgta ccagttagac tttccaaaaa ttgtgtgact tgtctggatc tgcaccacca ctgggtggta ccaaacccctt gtcaaactgg taggtgaaaa acggtcacca gatttagttt cagaactgtt tgtcatggaa agttttgtct taattgaagt attgtggttc tctagcaaat gccatttgta ctatattgaa atactttcat ttaatattat tttattcatt tgtggatata tacagtgact tataggcatt cttggaagtg cttttgttttg aatatttatg accttagaaa acagtcagtt ttactttata atgaagaatt gatacccttat tttctgtcac ttattattgc catcacccccc agtaaaaaagt acaagtgaat aaaacttaga tgagaactga ttaagaattt ctctatttcg gaataggcaa aatatttatg tttcttttggt atagagcttg cttgtctgta tgcctgatta aagactgtaa gaagatatta ttggctttat gtttacatta atgtttttata ttaaactgtt tttaactagc gaaaaaaaaa aaaaaaaaaa The complete ACAT2 amino acid sequence can be found under GENBANK® Accession No. AAH00408.1 (GI: 12653279) and is shown below (SEQ ID NO: 3):

mnagsdpvvi vsaartiigs fngalaavpv qdlgstvike vlkratvape dvsevifghv laagcgqnpv rqasvgagip ysvpawscom icgsglkavc lavqsigigd ssivvaggme nmskaphlay lrtgvkigem pltdsilcdg ltdafhnchm gitaenvakk wqvsredqdk vavlsqnrte naqkaghfdk eivpvlvstr rglievktde fprhgsniea msklkpyflt dgtgtvtpan asgindgaaa vvlmkksead krgltplari vswsqvgvep simgigpipa ikqavtkagw sledvdifei neafaavsaa ivkelglnpe kvnieggaia lghplgasgc rilvtllhtl ermgrsrgva alcigggmgi amcvqre The complete ACAT2 nucleic acid sequence can be found under GENBANK® Accession No. BC000408.2 (GI: 38197144) and is shown below (SEQ ID NO: 4):

ggagaagcaa gatgaatgca ggctcagatc ctgtggtcat cgtctcggcg gcgcggacca tcataggttc cttcaatggt gccttagctg ctgttcctgt ccaggacctg ggctccactg tcatcaaaga agtcttgaag agggccactg tggctccgga agatgtgtct gaggtcatct ttggacatgt cttggcagca ggctgtgggc agaatcctgt tagacaagcc agtgtgggtg caggaattcc ctactctgtt ccagcatgga gctgccagat gatctgtggg tcaggcctaa aagctgtgtg ccttgcagtc cagtcaatag ggataggaa ctccagcatt gtggttgcag gaggcatgga aaatatgagc aaggctcctc acttggctta cttgagaaca ggagtaaaga taggtgagat gccactgact gacagtatac tctgtgatgg tottacagat gcatttcaca actgtcatat gggtattaca gctgaaaatg tagccaaaaa atggcaagtg agtagagaag atcaggacaa ggttgcagtt ctgtcccaga acaggacaga gaatgcacg aaagctggcc attttgacaa agagattgta ccagttttgg tgtcaactag aagaggtctt attgaagtta aaacagatga gtttcctcgc catgggagca acatagaagc catgtccaag ctaaagcctt actttcttac tgatggaacg ggaacagtca ccccagccaa tgcttcagga ataaatgatg gtgctgcagc tgtggttctt atgaagaagt cagaagctga taaacgtgga cttacaccttt tagcacggat agtttctgg toccaagtgg gtgtgggagcc ttccattatg ggaataggac caattccagc cataaagcaa gctgttacaa aagcaggttg gtcactggaa gatgttgaca tatttgaaat caatgaagcc tttgcagctg tctctgctgc aatagttaaa gaacttggat taaacccaga gaaggtcaat attgaaggag gggctatagc cttgggccac cctcttggag catctggctg tcgaattctt gtgaccctgt tacacacact ggagagaatg ggcagaagtc gtggtgttgc agccctgtgc attgggggtg ggatgggaat agcaatgtgt gttcagagag aatgaattgc ttaaactttg aacaacctca atttctttt aaactaataa agtactaggt tgcaatatgt gaaatcagag gaccaaagta cagatggaaa ccatttccta catcacaaaa acccaagttt acagcttgta ctttactttta atgtgtaata ctcaactcaa ggtacaagac aattgcattt aacattgtta taaataaaag gaacatcaga tcaatcaaaa aaaaaaaaaa aaa The mouse ACAT1 shRNA sequence is shown below (SEQ ID NO:5):

CCGGCCAACCAGAGACUAAACAUAU-CUCGAGAUAUGUUUAGUCUCUGGUUG-GUUUUUUG

The mouse ACAT2 shRNA sequence is shown below (SEQ ID NO:6)

CCGGUGCGGUGGUUCAUGAGUAUAU-CUCGAGAUAUACUCAUGAACCACCG-CAUUUUUUG

In one embodiment, the ACAT inhibitor is a small molecule. Exemplary ACAT small molecule inhibitors include avasimibe (CI-1011) (Pfizer); CI-976; CP113,818 (Pfizer); pactimibe; NTE-122 (Nissin Food Products Co., Ltd); F-1394 (Fujirebio Inc.); PD140296 (Parke-Davis); PD128042 (Parke-Davis); PD132301-2 (Parke-Davis); octimibate; DuP128; 58-035; HL-004; SMP-500 (Sumitomo Pharmaceuticals Co.); CL-277,082; SKF-99085 (Glaxo Smith-Kline); CS-505 (Sankyo Pharma); eflucimibe, F12511; E5324; FR145237 (Fujisawa Pharmaceutical Co., Ltd.); CL277,082; YM-17E, FR129169 (Fujisawa Pharmaceutical Co., Ltd.); and tamoxifen.

Small molecule inhibitors that inhibit both ACAT1 and ACAT2 are also contemplated. ACAT non-selective small molecule inhibitors that inhibit both ACAT1 and ACAT2 may include, for example, avasimibe (CI-1011), CI-976 and pactimibe. Avasimibe is an oral ACAT non-selective inhibitor with $IC_{50}$ of 10 µM for ACAT1 and $IC_{50}$ of 2.5 µM for ACAT2). Avasimibe is generally considered safe when administered to rats, dogs, and humans. Although avasimibe effectively lowered hypercholesterolemia, orally administrated avasimibe showed no effect on body weight, food intake and insulin resistance.

In some embodiments, the small molecule is avasimibe, ([[2,4,6-tris(1-methylethyl)phenyl]acetyl]-, 2,6-bis(1-methylethyl)phenyl ester]sulfamic acid), a small molecule originally developed to control atherosclerosis. In some embodiments, the small molecule is CI-976, (2,2-Dimethyl- N-(2,4,6-trimethoxyphenyl) dodecanamide). CI-976 is an ACAT non-selective inhibitor with $IC_{50}$ of 5 μM for ACAT1 and $IC_{50}$ of <1 μM for ACAT2.

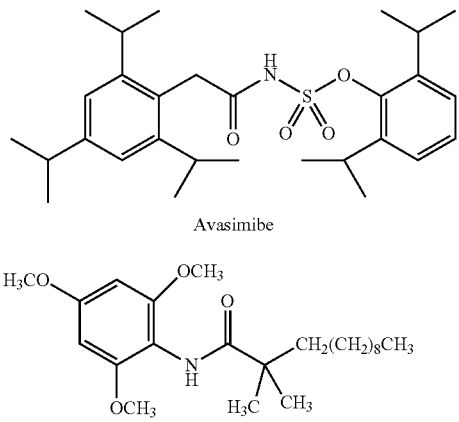

In the present invention, ACAT small molecule inhibitors have an $IC_{50}$ value in the range of 1 nM to 100 μM in vitro. When used in the methods of this invention as described herein, one or more ACAT inhibitors are administered to a subject (e.g., mammals, such as mice, rats, dogs, cats, horses, cows, and human) with the therapeutic benefit of decreasing, suppressing, reducing or ameliorating one or more signs or symptoms of obesity and/or T2D including, but not limited to, accumulation of fatty acids, triglycerides and/or LDs in adipose tissue and/or liver; weight of adipose tissue and/or liver; blood glucose, insulin, free fatty acids, cholesterol, LDL, leptin and/or cytokines; whole body weight in the subjects as compared to subjects not receiving treatment with ACAT inhibitor.

In some embodiments, the ACAT inhibitor is an antibody. The antibody of the present invention may be a polyclonal antisera or monoclonal antibody. The term antibody may include any of the various classes or sub-classes of immunoglobulin (e.g., IgG, IgA, IgM, IgD, or IgE derived from any animal, e.g., any of the animals conventionally used, e.g., sheep, rabbits, goats, or mice). Preferably, the antibody comprises a monoclonal antibody, e.g., an ACAT1 monoclonal antibody and/or an ACAT2 monoclonal antibody.

An "isolated antibody," as used herein, is intended to refer to an antibody that is substantially free of other antibodies having different antigenic specificities (e.g., an isolated antibody that specifically binds ACAT1 or that specifically binds ACAT2 and is substantially free of antibodies that specifically bind antigens other than ACAT1 or ACAT2). An isolated antibody that specifically binds ACAT1 or that specifically binds ACAT2 may, however, have cross-reactivity to other antigens, such as ACAT1 or ACAT2 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

An "antibody fragment" comprises a portion of an intact antibody, preferably the antigen binding and/or the variable region of the intact antibody. Examples of antibody fragments include Fab, Fab*, F(ab')2 and Fv fragments; diabodies; linear antibodies; single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding. i.e., it has a single antigen-binding site. Pepsin treatment of an antibody yields a single large F(ab')2 fragment, which roughly corresponds to two disulfide linked Fab fragments having different antigen-binding activity and is still capable of cross-linking antigen. Fab' fragments differ from Fab fragments by having a few additional residues at the carboxy terminus of the CH1 domain including one or more cysteines from the antibody hinge region. Fab'-SH is the designation herein for Fab' in which the cysteine residue (s) of the constant domains bear a free thiol group. F(ab')2 antibody fragments originally were produced as pairs of Fab' fragments which have hinge cysteines between them. Other chemical couplings of antibody fragments are also known.

In some embodiments, exemplary ACAT1 antibodies may include antibodies purchased from any suitable distributor, including, for example, Abcam, BD Biosciences, BioRad, Cell Signaling, EMD Milipore, Novus Biologicals, R&D Systems, and the like. For example, exemplary ACAT1 antibodies from Abcam may include, but are not limited to Aviva Systems Biology, Novus Biologicals, LifeSpan Biosciences, GeneTex, Abnova Corporation, Atlas Antibodies, GenWay Biotech, Invigrogen Antibodies, Sigma-Aldrich, and Biovision.

In some embodiments, exemplary ACAT2 antibodies may include antibodies purchased from any suitable distributor, including, for example, Abcam, BD Biosciences, BioRad, Cell Signaling, EMD Milipore, Novus Biologicals, R&D Systems, and the like. For example, exemplary ACAT2 antibodies from Abcam may include, but are not limited to Aviva Systems Biology, Novus Biologicals, LifeSpan Biosciences, GeneTex, Abnova Corporation, Atlas Antibodies, GenWay Biotech, Invigrogen Antibodies, Sigma-Aldrich, and Biovision.

In some embodiments, the ACAT inhibitor is an inhibitory nucleic acid. As used herein, "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene (e.g., ACAT1 and ACAT2). Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

Inhibitory nucleic acid, siRNA may refer to a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal. For example, they may be introduced systemically via the bloodstream. Such siRNAs are used to downregulate mRNA levels or promoter activity.

In some embodiments, the ACAT inhibitor is an inhibitory nucleic acid, wherein the inhibitory nucleic acid is shRNA.

Methods

The methods of the invention include administration of ACAT inhibitors (e.g., an antibody or fragment thereof, peptides, polypeptides or fragments thereof, small molecules, and an inhibitory nucleic acid) for suppressing food intake, reducing body weight; and treating or preventing a metabolic disease.

The therapeutic methods of the invention (which include prophylactic treatment) in general comprise administration of a therapeutically effective amount of the compounds herein, such as a compound of the formulae herein to a subject in need thereof, including a mammal, particularly a human. Such treatment will be suitably administered to subjects, particularly humans, suffering from, having, susceptible to, or at risk for a metabolic disease or symptom thereof. Determination of those subjects "at risk" can be made by any objective or subjective determination by a diagnostic test or opinion of a subject or health care provider (e.g., genetic test, enzyme or protein marker, family history, and the like).

The term "therapeutically effective amount" refers to an amount of an ACAT inhibitor administered sufficient to suppress food intake, suppress body weight; and treat, ameliorate a symptom of, reduce the severity of, or reduce the duration of metabolic diseases that are related to accumulation of free fatty acids, TG and CE by the action of ACAT (e.g., T2D and obesity). In some embodiments, the therapeutically effective amount is in an amount effective to achieve one or more of the following: inhibit lipid droplet size accumulation in adipose tissue and inhibit enzymes that catalyze the conversion of free cholesterol to cholesterol ester (e.g., acyl-coenzyme A:cholesterol acyltransferase 1 (ACAT1) and acyl-coenzyme A:cholesterol acyltransferase 2 (ACAT2). Additionally, the therapeutically effective amount may decrease or suppress lipid accumulation (e.g., in adipose tissue), decrease or suppress overall food intake, decrease or suppress blood glucose, decrease or suppress blood insulin, improves insulin sensitivity, and decrease or suppress leptin. In some embodiments, the therapeutically effective amount is in an amount effective to decrease, suppress, reduce or ameliorate one or more signs or symptoms of obesity including, but not limited to, accumulation of fatty acids, triglycerides and/or LDs in adipose tissue and/or liver; weight of adipose tissue and/or liver; blood glucose, insulin, free fatty acids, cholesterol, LDL, leptin and/or cytokines; or whole body weight in the subjects as compared to subjects not receiving treatment with ACAT inhibitor.

Dosages of the ACAT inhibitors may be varied depending upon the requirements of the patient. Utilizing the teachings provided herein, an effective prophylactic or therapeutic treatment regimen can be planned that does not cause substantial toxicity and yet is effective to treat the clinical symptoms demonstrated by the particular patient. The dose administered to a patient should be sufficient to affect a beneficial therapeutic response in the patient over time. The size of the dose also will be determined by the existence, nature, and extent of any adverse side-effects. Determination of the proper dosage for a particular situation is within the skill of the art. This planning should involve the careful choice of the ACAT inhibitor by considering factors such as compound potency, relative bioavailability, patient body weight, presence and severity of adverse side effects. Generally, treatment is initiated with smaller dosages which are less than the optimum dose of the ACAT inhibitor. Thereafter, the dosage is increased by small increments until the optimum effect under circumstances is reached. Dosage amounts and intervals can be adjusted individually to provide levels of the ACAT inhibitor effective for the particular clinical indication being treated. This will provide a therapeutic regimen that is commensurate with the severity of the individual's disease state.

The dosage and frequency (single or multiple doses) of the ACAT inhibitors administered to a subject can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms and severity of such symptoms), kind of concurrent treatment, complications from the disease being treated or other health-related problems. Dosages can be provided in mg/kg/day units of measurement (which dose may be adjusted for the patient's weight in kg, body surface area in m2, and age in years). Other therapeutic regimens or agents can be used in conjunction with the methods and the ACAT inhibitors described herein. Adjustment and manipulation of established dosages (e.g., frequency and duration) are well within the ability of those skilled in the art.

For any composition and the ACAT inhibitors described herein, the therapeutically effective amount can be initially determined from cell culture assays. Target concentrations will be those concentrations of the ACAT inhibitors that are capable of achieving the methods described herein, as measured using the methods described herein or known in the art. As is well known in the art, effective amounts of the ACAT inhibitors for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

In some embodiments, an effective amount can range from about 0.001 mg/kg to about 1000 mg/kg, more preferably 0.01 mg/kg to about 100 mg/kg, more preferably 0.1 mg/kg to about 10 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg. 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents. In some embodiments, a therapeutically effective dose typically varies from 0.01 mg/kg/day to approximately 750 mg/kg/day. In some embodiments, a therapeutically effective dose is from about 0.01 mg/kg/day to about 200 mg/kg/day.

In some embodiments, the methods may comprise administering the ACAT inhibitor according to a specified dosing schedule or therapeutic regimen. For example, the ACAT inhibitor can be administered once daily or from two to five times daily. In some embodiments, the ACAT inhibitor is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks. In some embodiments, the ACAT inhibitor is administered for at least 25 days. In some embodiments, the ACAT inhibitor is administered for at least 14 days. In some embodiments, the ACAT inhibitor is administered for at least 8 days. In some embodiments, the ACAT inhibitor is administered for at least 6 days.

In some embodiments, the methods may comprise administering the ACAT inhibitor systemically or locally by oral administration, subcutaneous injection, intraperitoneal injection, intravenous injection, rectal administration, topical application or inhalation.

Compositions

The present invention provides pharmaceutical compositions comprising an effective amount of an ACAT inhibitor (e.g., an antibody or fragment thereof, peptides, polypeptide or fragments thereof, small molecules, and inhibitory nucleic acids) and at least one pharmaceutically acceptable excipient or carrier, wherein the effective amount is as described above in connection with the methods of the invention. In accordance with any of the embodiments described here, the pharmaceutical composition may be adapted for oral, buccal, or parenteral, subcutaneous, intraperitoneal, intravenous, rectal or topical administration or inhalation. In some embodiments, the pharmaceutical composition is adapted for oral administration. In some embodiments, the pharmaceutical composition is adapted for parenteral administration. In some embodiments, the pharmaceutical composition is adapted for intravenous injection. In some embodiments, the composition may comprise at least two ACAT inhibitors (e.g., avasimibe and CI-976) as the active agents.

A "pharmaceutical composition" is a formulation containing the compounds described herein in a pharmaceutically acceptable form suitable for administration to a subject. The term "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Additionally, "pharmaceutically acceptable" means approved or approvable by a regulatory agency of the Federal or a state government or the corresponding agency in countries other than the United States, or that is listed in the U.S. Pharmacopoeia or other generally recognized pharmacopocia for use in animals, and more particularly, in humans.

As used herein, "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. Pharmaceutically acceptable carriers include sterile aqueous solutions or dispersions and sterile powders for the extemporaneous preparation of sterile topical solutions or dispersion. The use of such media and agents for pharmaceutically active substances is well known in the art. "Pharmaceutical carriers" or "carriers" as used herein can further include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™., polyethylene glycol (PEG), and Pluronics™.

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). The active therapeutic agent(s) may also be incorporated into microspheres, microcapsules, nanoparticles, liposomes, or the like for controlled release. For example, a pharmaceutical composition of the invention may be in the form of an aqueous solution or powder for aerosol administration by inhalation, in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

A pharmaceutical composition can be in the form of a sterile aqueous solution or dispersion suitable for administration by either parenteral administration or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present disclosure as a free base or pharmacologically acceptable salt can be prepared in water suitably mixed with a surfactant. Examples of suitable surfactants are given below.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The term parenteral as used herein includes subcutaneous, intracutaneous, intravenous, intramuscular, intra-articular, intraarterial, intrasynovial, intrasternal, intrathecal, intralesional and intracranial injection or infusion techniques. For parenteral administration in an aqueous solution, for example, the solution should be suitably buffered and the liquid diluent first rendered isotonic with sufficient saline or glucose. Sterile injectable solutions can be prepared by incorporating the active compounds in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. Aqueous solutions, in particular, sterile aqueous media, are especially suitable for intravenous, intramuscular, subcutaneous and intraperitoneal administration. These solutions are sterile and generally free of undesirable matter. These compositions may be sterilized by conventional, well known sterilization techniques. For example, one dosage could be dissolved in 1 ml of isotonic NaCl solution and either added to 1000 ml of hypodermoclysis fluid or injected at the proposed site of infusion.

The compositions may contain pharmaceutically acceptable auxiliary substances as required to approximate physiological conditions such as stabilizing, tonicity adjusting, pH adjusting and buffering agents, toxicity adjusting agents and the like, for example, sodium acetate, sodium chloride, potassium chloride, calcium chloride, sodium lactate hydrochloric acid, sodium hydroxide, 1,3-butanediol, Ringer's solution, isotonic sodium chloride solution, dextrose solution and the like. The concentration of active agent in these formulations can vary, and will be selected primarily based on fluid volumes, viscosities, body weight and the like in accordance with the particular mode of administration selected and the subject's needs. Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative (e.g., methyl, ethyl or n-propyl p-hydroxybenzoate) to prevent the growth of microorganisms. Such compositions are well known to those skilled in the art of pharmaceutical formulation. Formulations can be found in Remington: The Science and Practice of Pharmacy, supra. In cases where one of the compounds is only sparingly or slightly soluble in water, a dissolution enhancing or solubilizing agent can be added, or the solvent may include 10-60% w/w of propylene glycol or the like. The preparation of more, or highly, concentrated solutions for direct injection is also contemplated. DMSO can be used as solvent for extremely rapid penetration, delivering high concentrations of the active agents to a small area.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

The pharmaceutical compositions for use in the methods of the present disclosure can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the disclosure are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The formulations of compounds can be presented in bulk or unit-dose (e.g., in single-dose ampoules) or multi-dose sealed containers in which a suitable preservative may be added, such as ampules and vials. It is especially advantageous to formulate pharmaceutical compositions in dosage unit form for case of administration and uniformity of dosage. Thus, the composition can be in unit dosage form. In such form the preparation is subdivided into unit doses containing appropriate quantities of the active component. The compositions can be administered in a variety of unit dosage forms depending upon the method of administration. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. A dosage unit form include, but are not limited to, an ampoule, a vial, a suppository, a powder, a tablet, a pill, a capsule, a lozenge, an IV bag, or a single pump on an aerosol inhaler.

Combination Therapies

The present invention also provides methods comprising combination therapy. As used herein, the terms "combination therapy" or "co-therapy" include the administration of a therapeutically effective amount of an ACAT inhibitor, with at least one additional active agent, as part of a specific treatment regimen intended to provide a beneficial effect from the co-action of the active agents in the regimen. Thus, the invention provides methods of treating a subject for obesity or T2D using a combination therapy comprising an ACAT inhibitor and at least one additional active agent in a regimen for the treatment of the metabolic disease (e.g., overweight, obesity, diabetes, T2D or related diseases).

The at least one additional active agent may be a therapeutic agent, for example, an anti-inflammatory, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds.

Non-limiting examples of anti-inflammatory agents include 21-acetoxypregnenolone, alclometasone, algestone, amcinonide, betamethosone diproprionate, budesonide, chloroprednisone, clobetasol, corticosterone, cortisone, cortivazol, deflazacort, desonide, dexamethasone alcohol, dexamethasone sodium phosphate, diflorasone, dutasteride, flumethasone pivalate, fluocinonide, fluorometholone acetate, fluorometholone alcohol, fluticasone propionate, halcinonide, halobetasol propionate, halometasone, halopredone acetate, hydrocortamate, hydrocortisone, hydroflumethiazide lotoprendol etabonate, medrysone, prednisolone acetate, prednisolone sodium phosphate, rimexolone, hydrocortisone, hydrocortisone actetate, lodoxamide tromethamine, difluprednate, or a combination thereof. In one aspect, the steroidal anti-inflammatory agent may be a corticosteroid drug, such as prednisolone acetate.

The anti-inflammatory agents may be used in any suitable amounts. For example, in some embodiments, such anti-inflammatory agents may be in a concentration of from about 0.01% to 10.0% by weight. The anti-inflammatory agents can be present at about 0.01, 0.1, 0.2, 0.3, 0.4, 0.5, 1.0, 2.0, 5.0, and 10 percent by weight or any amount in between these amounts. In some embodiments, the anti-inflammatory may be in a concentration of about 0.05% (w/v) to about 1.0% (w/v).

A "combined synergistic amount" as used herein refers to the sum of a first amount (e.g., an amount of an ACAT inhibitor) and a second amount (e.g., an amount of an anti-inflammatory agent) that results in a synergistic effect (i.e., an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

A "combined additive amount" as used herein refers to the sum of a first amount (e.g., an amount of an ACAT inhibitor) and a second amount (e.g., an amount of an anti-inflammatory agent) that results in an additive effect (i.e., an effect equal to the sum of the effects). Therefore, the terms "additive", "combined additive amount", and "additive therapeutic effect" which are used herein interchangeably, refer to a measured effect of compounds administered in combination where the measured effect is equal to the sum of the individual effects of each of the compounds administered alone as a single agent.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

The combined administrations contemplates co-administration, using separate formulations or a single pharmaceutical formulation, and consecutive administration in either order, wherein preferably there is a time period while both (or all) active agents simultaneously exert their biological activities.

EXAMPLES

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Figure 2:
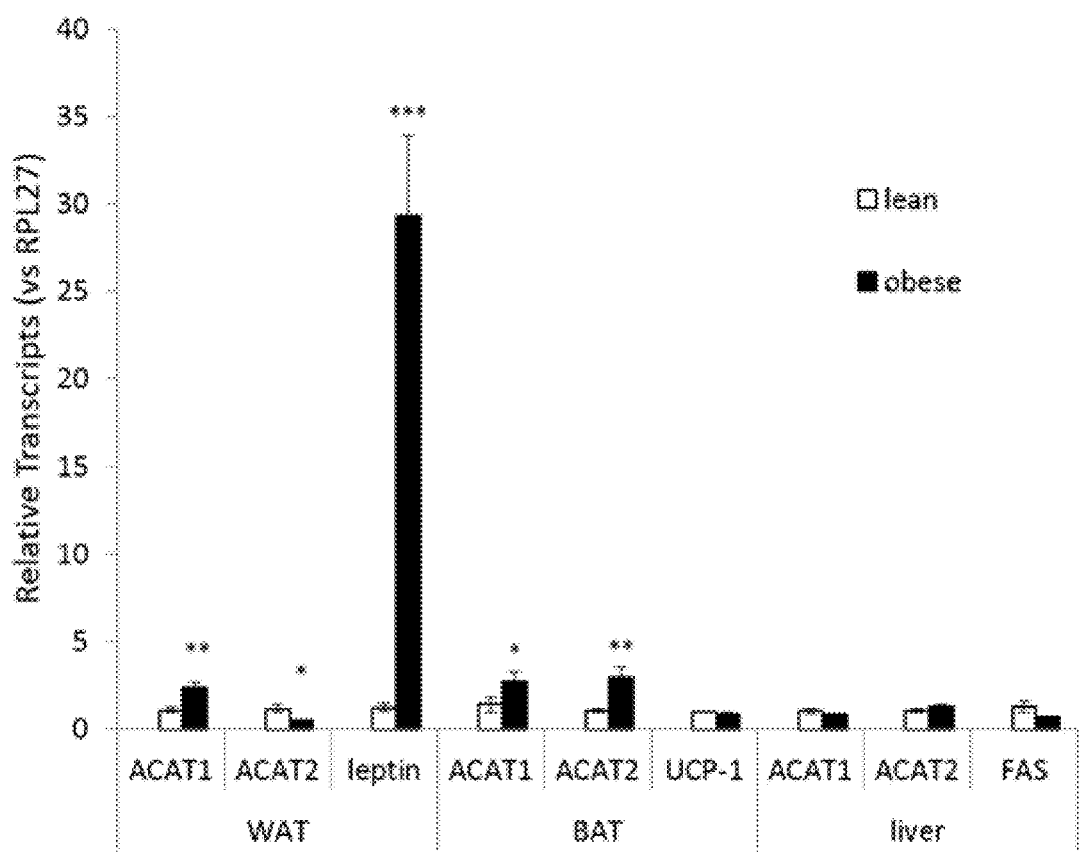
FIG. 2 is a bar graph showing the transcript levels of ACAT1, ACAT2, leptin, UCP-1 and FAS relative to RPL27 in white adipose tissue (WAT), brown adipose tissue (BAT) and the liver of lean mice and high fat diet-induced obese mice.

Example 1: A Positive Correlation of ACAT1 Expression with Adipogenesis and Obesity To examine the function of ACATs in obesity, the expression patterns of ACAT1 and ACAT2 genes, and their gene products during adipogenesis of murine 3T3-L1 preadipocytes in vitro were examined. ACAT1 mRNA level was markedly increased in adipocytes from 2 days after initiation of adipogenesis (i.e., D2) as judged by real-time PCR assay (FIG. 1). However, ACAT2 mRNA level was similar between preadipocytes (DO) and mature adipocytes (D6) while a temporal reduction of ACAT2 level was observed at D2 (FIG. 1). In addition, white adipose tissue (WAT) isolated from high fat diet-induced obese mice displayed elevated mRNA level of ACAT1 and reduced mRNA level of ACAT2 when compared with those in lean mice as judged by real-time PCR assay. Leptin level was measured in WAT from lean and obese mice to ensure the development of obesity (FIG. 2). In addition, brown adipose tissue (BAT) from obese mice exhibited elevated levels of both ACAT1 and ACAT2. Uncoupling protein-1 (UCP-1) level was measured in BAT from lean and obese mice as a BAT-specific marker protein (FIG. 2). However, liver from lean and obese mice exhibited similar levels of ACAT1 and ACAT2 (FIG. 2).

Example 2: Inhibition of Lipid Accumulation in Adipocytes by ACAT Inhibitors (Avasimibe and CI-976)

Figure 3A:
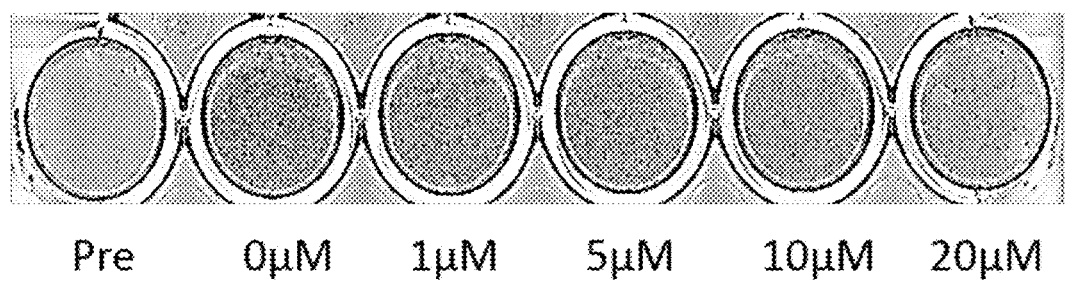
FIG. 3A is an image showing lipid accumulation in preadipocytes and mature adipocytes differentiated in the presence of various concentrations of avasimibe, visualized by Oil Red O staining.
Figure 3B:
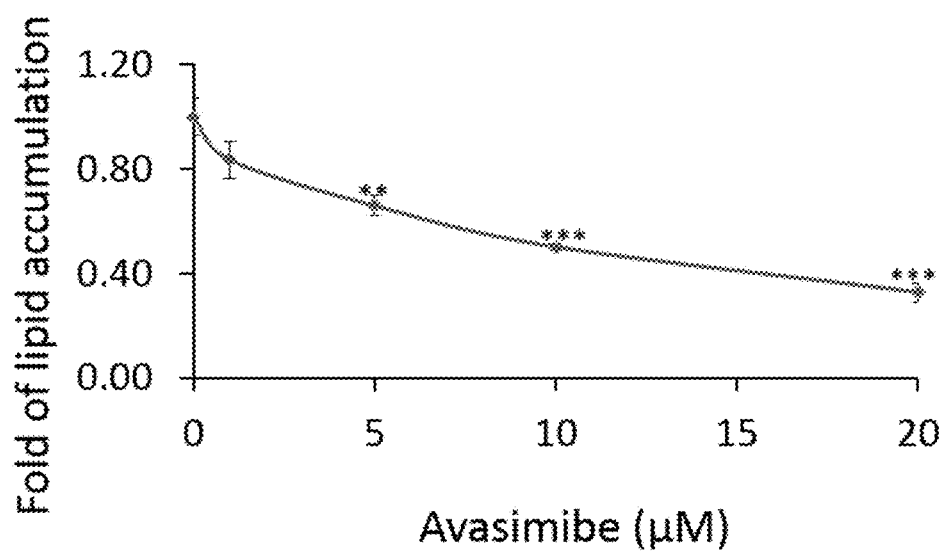
FIG. 3B is a bar graph showing the quantified Oil Red O stained-lipid accumulation shown in FIG. 3A.
Figure 4:
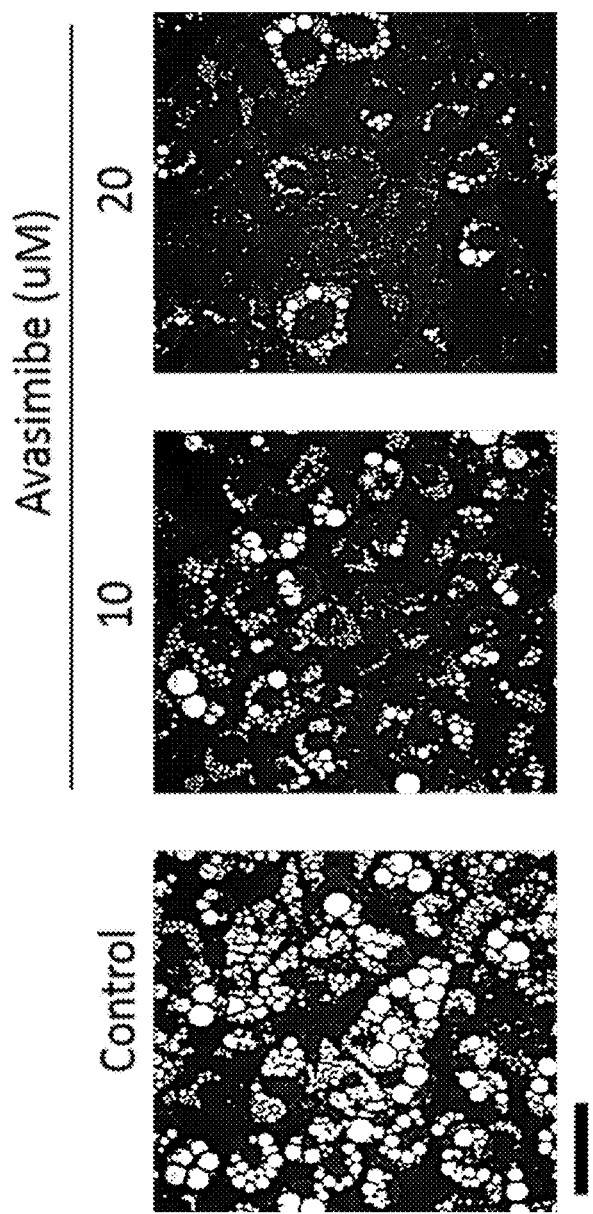
FIG. 4 is a Coherent Anti-Stokes Raman Scattering (CARS) microscopy image showing the suppressed lipid accumulation by avasimibe in mature adipocytes.
Figure 5A:
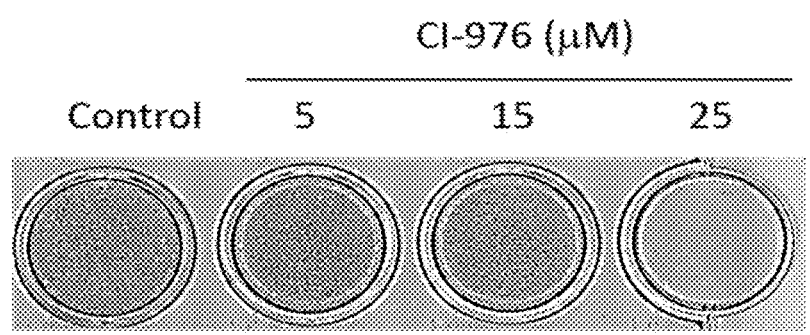
FIG. 5A is an image showing lipid accumulation in preadipocytes and mature adipocytes differentiated in the presence of various concentrations of CI-976, visualized by Oil Red O staining.
Figure 5B:
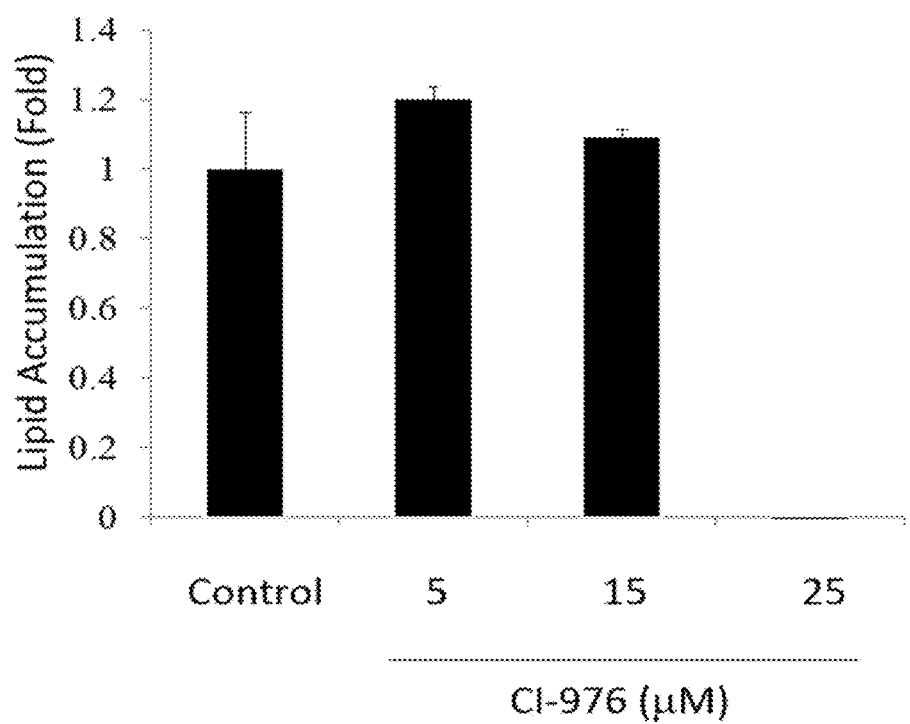
FIG. 5B is a bar graph showing the quantified Oil Red O stained-lipid accumulation shown in FIG. 5A.

To determine the effect of ACAT inhibitors on lipid accumulation in adipocytes, murine 3T3-L1 preadipocytes were differentiated to mature adipocytes in the presence or absence of avasimibe (0 µM, 1 µM, 5 µM, 10 µM and 20 µM) for 6 days. Avasimibe solution was prepared by dissolving in dimethyl sulfoxide (DMSO). At day 6, preadipocytes and avasimibe-treated differentiated adipocytes were subjected to Oil Red O staining to visualize accumulated intracellular lipids. Oil Red O stained lipids were then extracted for spectrometric quantification of lipids. Intracellular lipids were decreased in a dose-dependent manner by up to 60% (FIG. 3A and FIG. 3B). Avasimibe-inhibited lipid accumulation was confirmed by Coherent Anti-Stokes Raman Scattering (CARS) microscopy, which is a dye-free non-invasive imaging technique for visualization of lipid-containing molecules in biological systems (FIG. 4). Similar with avasimibe, treatment of differentiating adipocytes with CI-976, a non-selective ACAT inhibitor, for 6 days in the concentration range of 0 µM, 5 µM, 15 µM and 20 µM also resulted in a decrease in lipid accumulation as judged by Oil Red O staining (FIG. 5A and FIG. 5B). Thus, these data indicate that avasimibe and CI-976 were effective in markedly reducing or suppressing lipid droplet accumulation in differentiating adipocytes in vitro.

Figure 6:
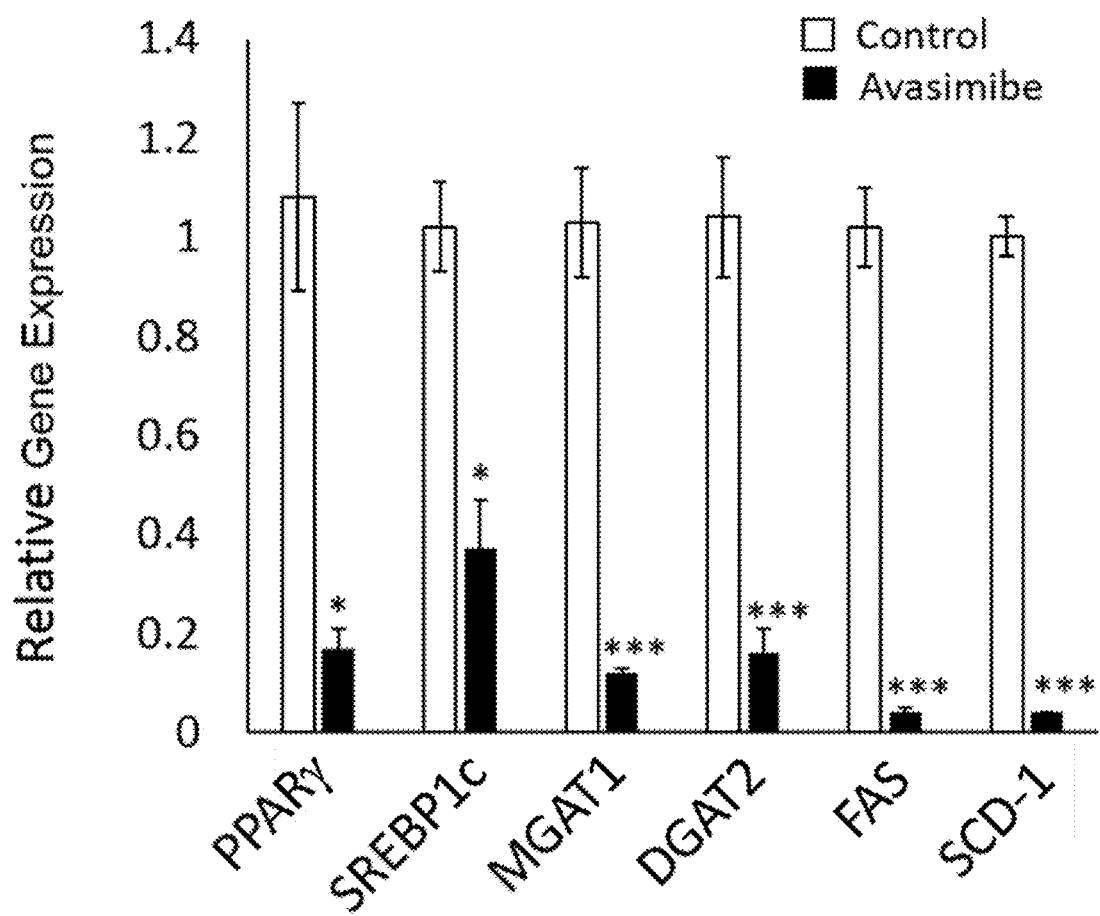
FIG. 6 is a bar graph showing that avasimibe suppresses mRNA levels of genes involved in lipid synthesis in adipocytes.

To characterize the effect of avasimibe treatment on mRNA levels of genes involved in lipid metabolism and adipocyte function, differentiated 3T3-L1 preadipocytes in the presence or absence of avasimibe (20 µM) for 6 days were subjected to real-time PCR assay for the analysis of expression of genes involved in synthesis of fatty acids and TGs such as PPARγ, sterol regulatory element binding protein 1c (SREBP1c), MGAT1, DGAT2, FAS and SCD-1. As shown in FIG. 6, avasimibe treatment resulted in a marked decrease in mRNA levels of genes involved in lipid synthesis in adipocytes.

Figure 7:
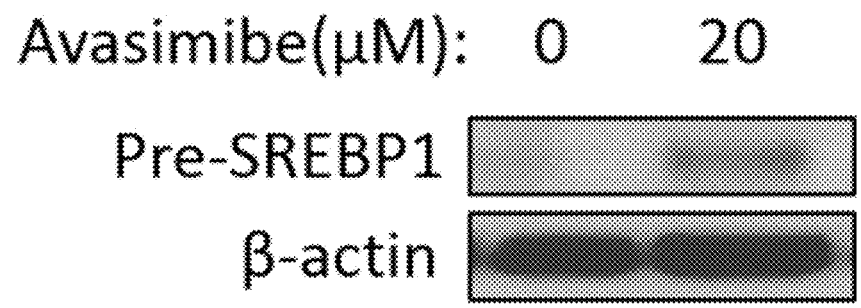
FIG. 7 is a Western blotting image showing that avasimibe increases the level of the 125 kDa inactive precursor form of SREBP1 in adipocytes.

Example 3: Avasimibe Lowers Lipid Accumulation in Adipocytes Through Modulation of SREBP1 Expression and Function on Lipid Synthesis Because SREBP1 plays a key role in de novo fatty acids and TG synthesis and the data in FIG. 6 show a potential inhibitory role of avasimibe in suppression of SREBP1-downstream genes involved in fatty acid and TG synthesis, the ability of avasimibe treatment to alter SREBP1 protein expression and de novo fatty acid synthesis in adipocytes was tested. Avasimibe treatment resulted in elevated levels of the 125 kDa inactive precursor form of SREBP1 in adipocytes as judged by Western blot analysis using antibodies specific to SREBP1 and β-actin (a protein loading control) (FIG. 7).

Figure 8:
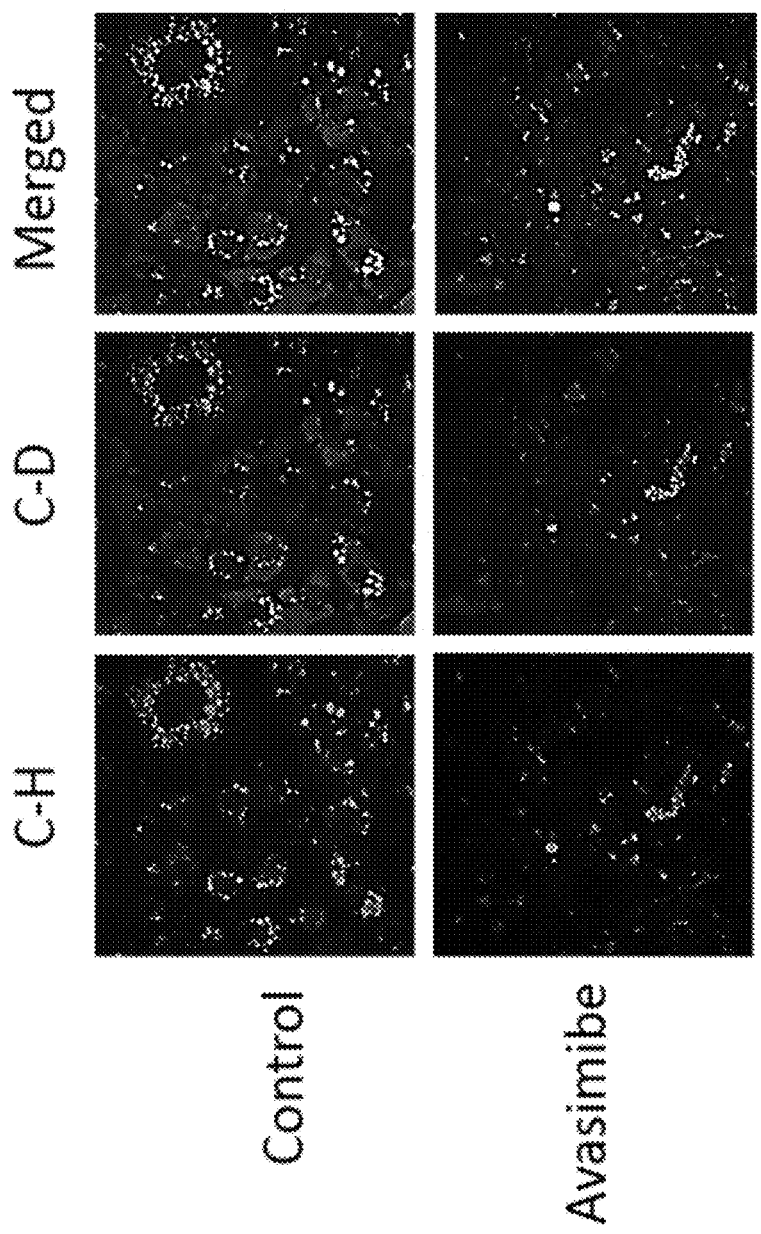
FIG. 8 is a stimulated Raman scattering (SRS) microscopy image showing the suppressive role of avasimibe in de novo fatty acid synthesis in adipocytes.

Using deuterium labeled glucose-d7, the effect of avasimibe on de novo fatty acid synthesis in adipocytes treated with or without avasimibe was examined. Glucose-d7 incorporated fatty acids were visualized by stimulated Raman scattering (SRS) microscopy. SRS imaging showed reduced level of LD accumulation (i.e., vibrational image of C—H bond-rich lipid molecules) and the signal intensity of glucose-d7 accumulated in the LDs as a result of replacement of all the hydrogen atoms in fatty acids by glucose-derived deuterium atoms (i.e., vibrational image of C-D bond-rich lipid molecules) in avasimibe-treated adipocytes (FIG. 8). These results indicate an inhibitory or suppressive role of avasimibe in de novo fatty acid synthesis potentially through inhibition of SREBP1 function.

Example 4: Effect of Avasimibe on Cholesterol Metabolism in Adipocytes

Figure 9:
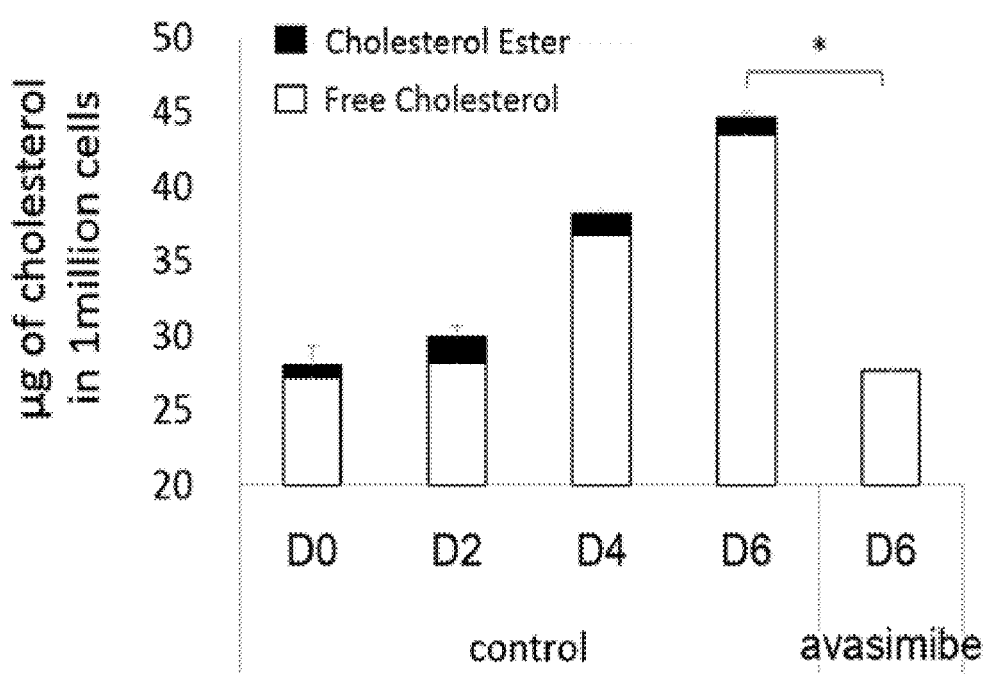
FIG. 9 is a bar graph showing that avasimibe completely inhibits cholesterol ester (CE) accumulation and suppresses the cholesterol level in adipocytes during adipogenesis.
Figure 10:
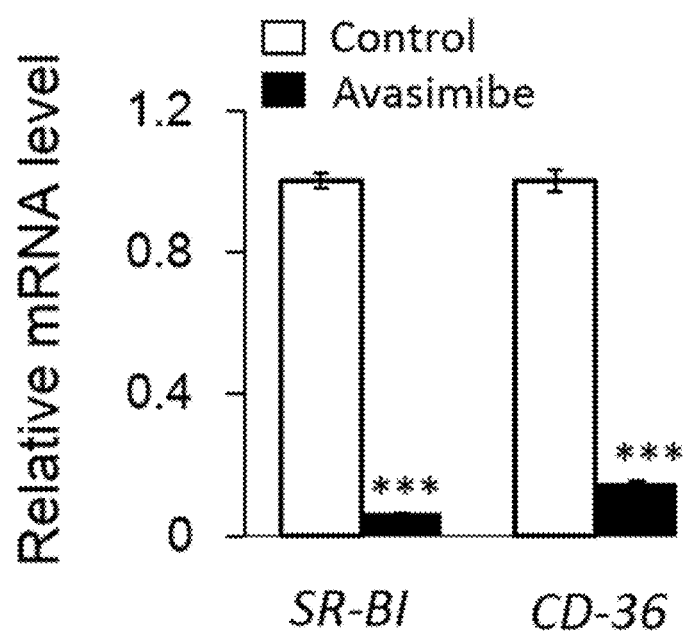
FIG. 10 is a bar graph showing that avasimibe suppresses the relative mRNA levels of SR-BI and CD-36 in adipocytes.
Figure 11:
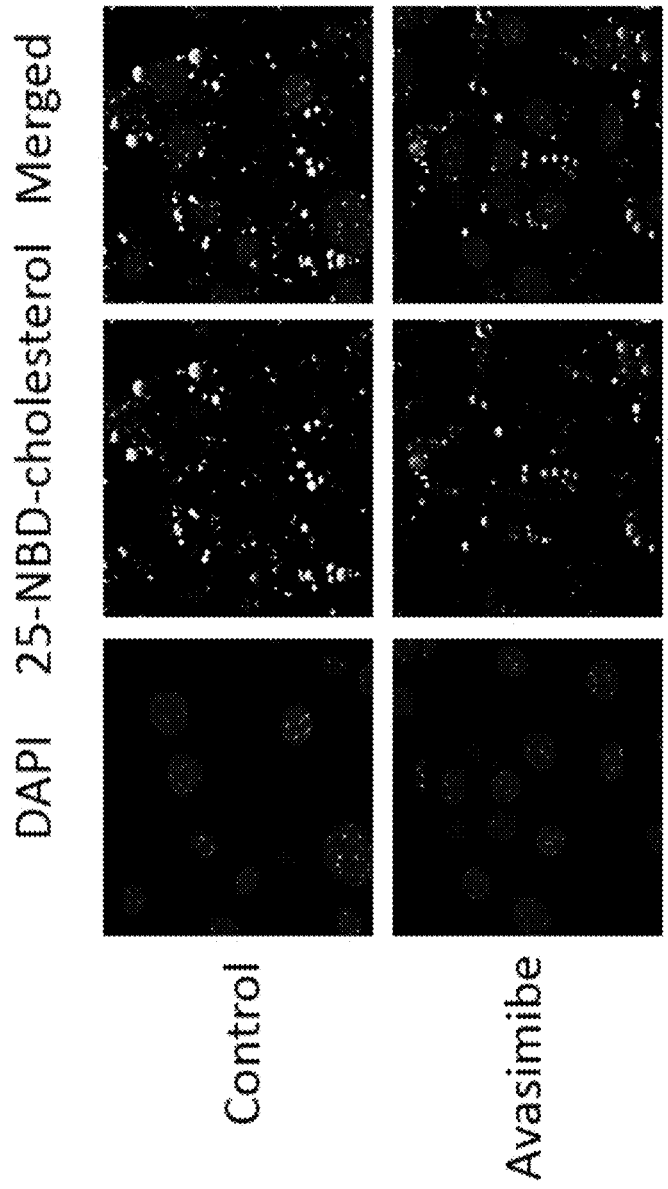
FIG. 11 is an image of the 25-[N-[(7-nitro-2-1,3-benzoxadiazol-4-yl)methyl]amino]-27-norcholesterol (25-NBD cholesterol)-based ACAT assay showing that avasimibe suppresses the ACAT activity and thereby suppresses accumulation of fluorescence-labeled CE in adipocytes.

Previous studies reported an adipogenesis-dependent increase in cholesterol accumulation in adipocytes. Similarly, adipogenesis was associated with elevated level free cholesterol with little change in CE level. Moreover, avasimibe treatment resulted in a significantly reduced level of cholesterol and a complete inhibition of CE accumulation in adipocytes during adipogenesis (FIG. 9). This was accompanied by a marked decrease in mRNA levels of genes involved in cholesterol uptake such as scavenger receptor class B member 1 (SR-BI) and CD-36 in adipocytes treated with avasimibe when compared with those in control adipocytes (FIG. 10). Using a 25-[N-[(7-nitro-2-1,3-benzoxadiazol-4-yl)methyl]amino]-27-norcholesterol (25-NBD cholesterol)-based ACAT assay, avasimibe indeed inhibited the ACAT activity, thereby lowering accumulation of fluorescence-labeled CE in adipocytes (FIG. 11). Collectively, the results indicate that avasimibe not only inhibits synthesis of fatty acids and TGs, but also inhibits cholesterol uptake and accumulation of free cholesterol and CE in adipocytes, possibly through suppression of expression of genes involved in cholesterol uptake from the medium.

Figure 12:
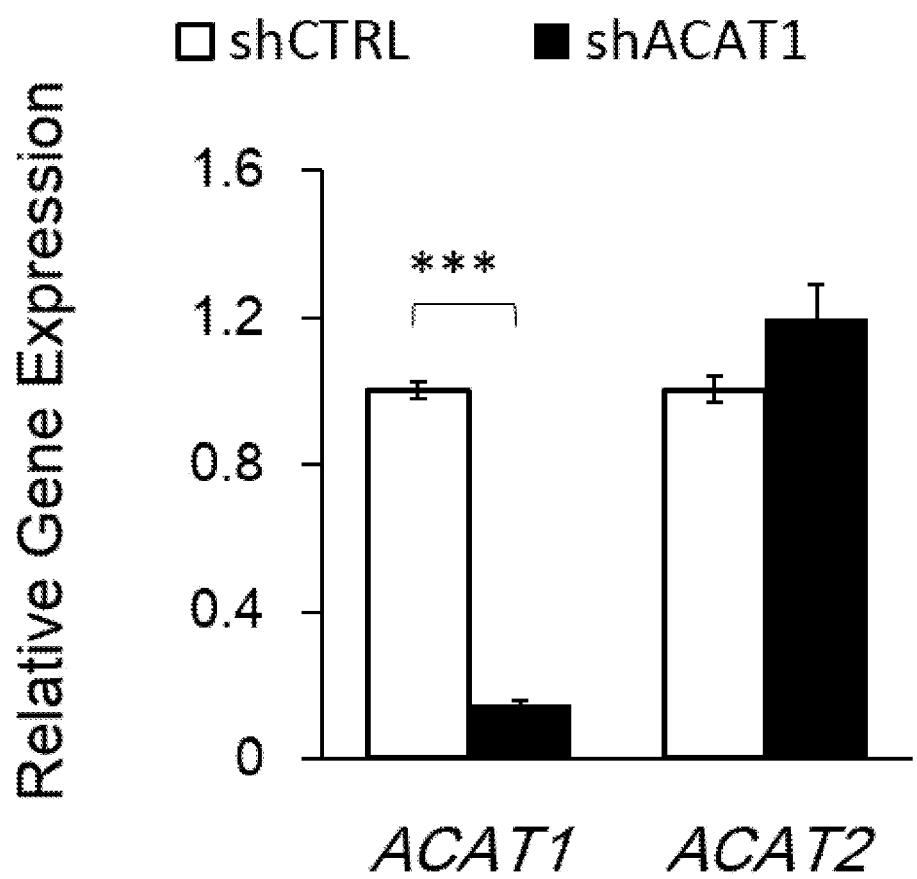
FIG. 12 is a bar graph showing the efficiency of the ACAT1 shRNA to knockdown the ACAT1 expression without altering the ACAT2 expression level in adipocytes.
Figure 13A:
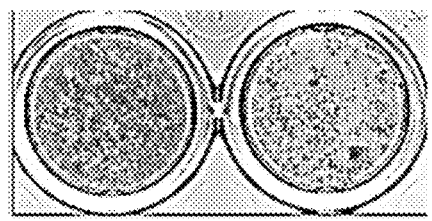
FIG. 13A is an image showing the effect of ACAT1 knockdown on lipid accumulation in adipocytes, visualized by Oil Red O staining.
Figure 13B:
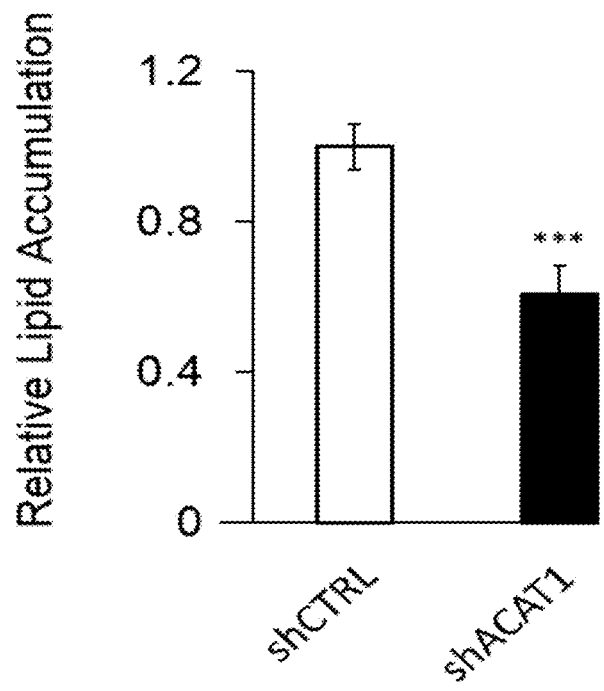
FIG. 13B is a bar graph showing the quantified Oil Red O stained-lipid accumulation shown in FIG. 13A.
Figure 14:
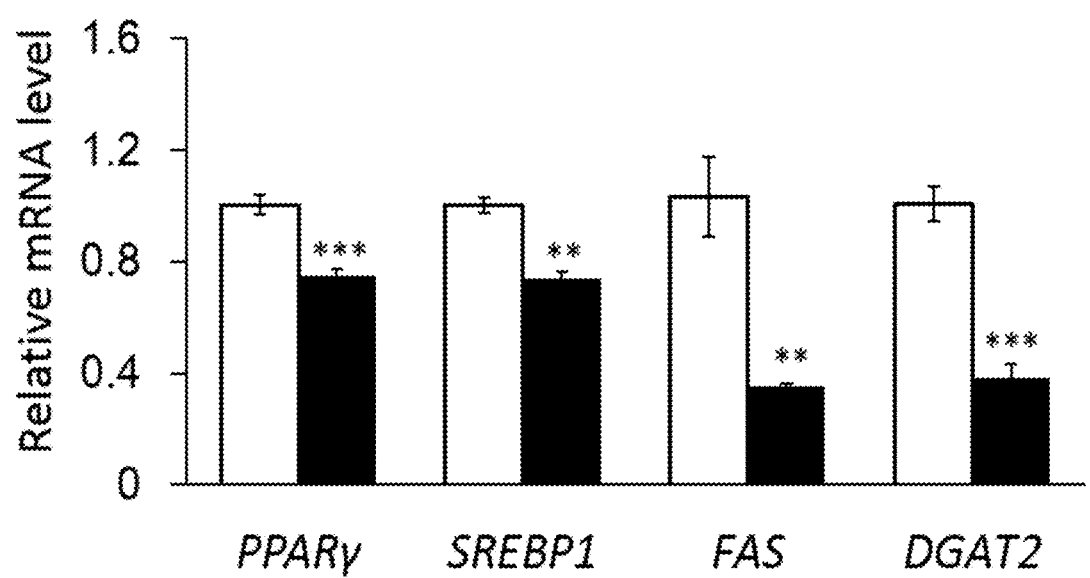
FIG. 14 is a bar graph showing that ACAT1 knockdown reduces mRNA levels of genes involved in lipid synthesis in adipocytes.
Figure 15A:
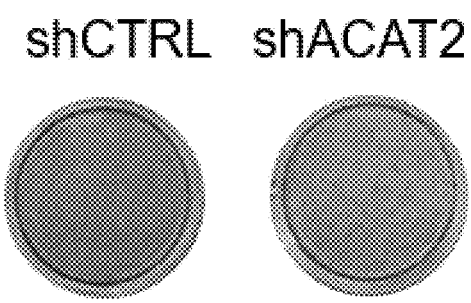
FIG. 15A is an image showing the effect of ACAT2 knockdown on lipid accumulation in adipocytes, visualized by Oil Red O staining.
Figure 15B:
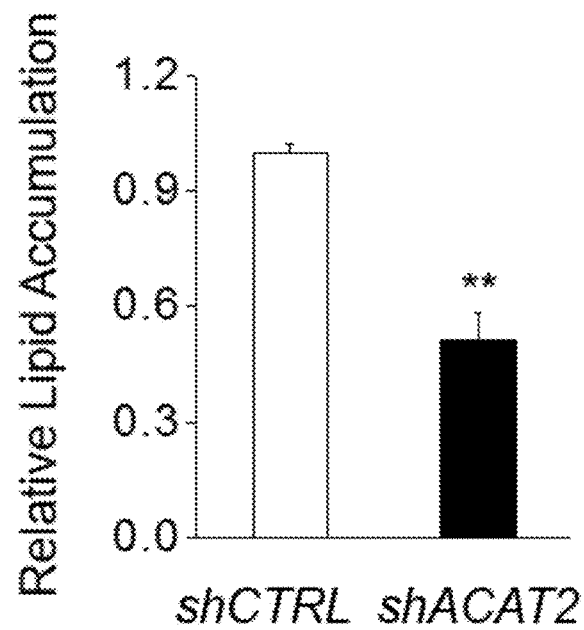
FIG. 15B is a bar graph showing the quantified Oil Red O stained-lipid accumulation shown in FIG. 15A.
Figure 16:
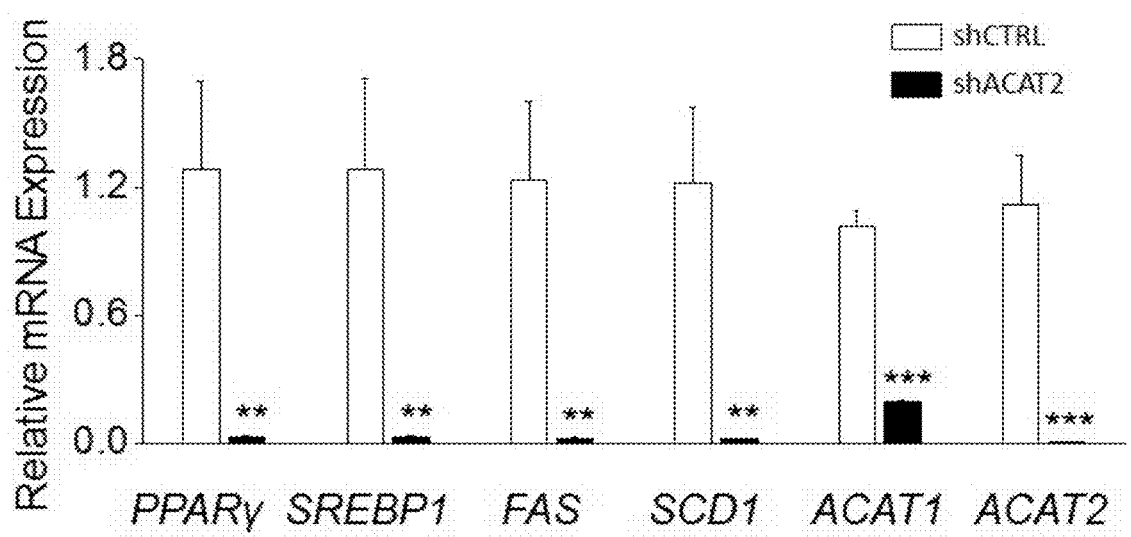
FIG. 16 is a bar graph showing that ACAT2 knockdown reduces mRNA levels of genes involved in lipid synthesis in adipocytes.

Example 5: Effect of shRNA Inhibition of ACAT1 on Lipid Droplet Accumulation in Adipocytes The direct role of ACAT1 on synthesis of fatty acids and TGs in adipocytes by lentivirus-mediated ACAT1 knockdown using its specific shRNA was tested. FIG. 12 shows a gene knockdown efficiency of the shRNA to ACAT1 with no influence on ACAT2 expression level in adipocytes. Similar with the effect of avasimibe on adipocytes, ACAT1 knockdown resulted in suppression of lipid accumulation in adipocytes up to 40% than control ShRNA adipocytes as judged by Oil Red O staining (FIG. 13A and FIG. 13B), and a marked decrease in mRNA levels of genes involved in lipid synthesis as indicated by real-time PCR assay (FIG. 14). Similarly, ACAT2 knockdown resulted in suppression of lipid accumulation in adipocytes up to 55% than control ShRNA adipocytes as judged by Oil Red O staining (FIG. 15A and FIG. 15B). ACAT2 knocking down resulted in a dramatic reduction in mRNA levels of genes involved in TG synthesis (FIG. 16). Here, ACAT inhibitors, avasimibe and CI-976, have been identified to be highly effective for anti-obesity treatment in a mouse model of obesity. The cell-based studies indicated that ACAT inhibition and ACAT1 knockdown reduced or suppressed synthesis of fatty acid, TG and lipid droplets in adipocytes with lower level of accumulation of free cholesterol and CE. The cell-based studies also suggest that the inhibitory or suppressive role of ACAT inhibition and ACAT1 knockdown in lipid synthesis in adipocytes is largely due to suppression of SREBP1 expression and function, and expression of its-downstream genes involved in synthesis of fatty acids and TG.

Figure 17A:
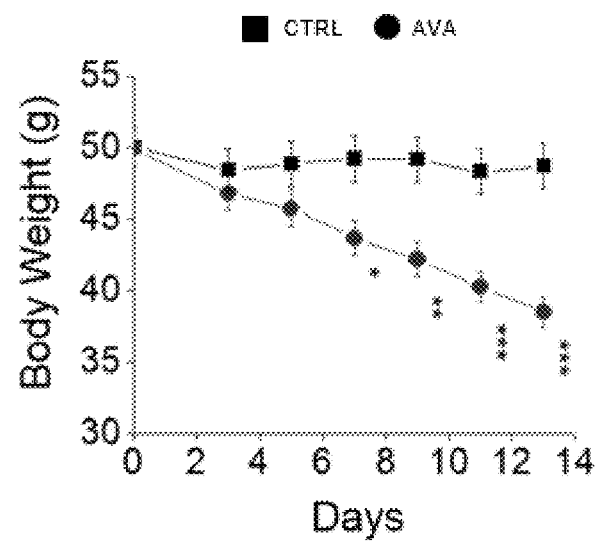
FIG. 17A is a graph showing the progressive loss of body weight by avasimibe in a high-fat diet-induced obesity mouse model.
Figure 17B:
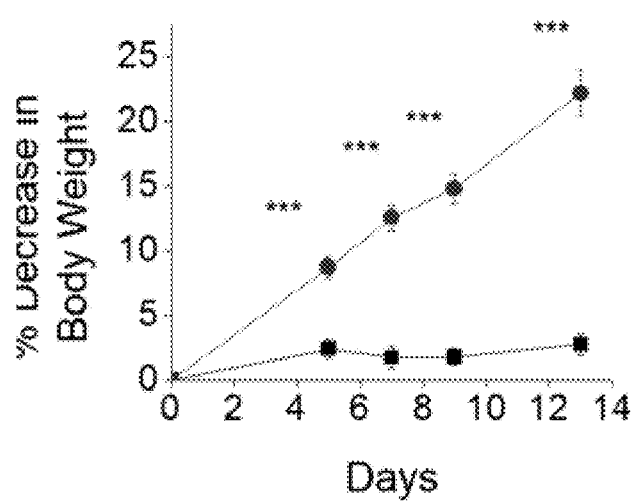
FIG. 17B is a graph representing the percentage of the body weight loss by avasimibe in a high-fat diet-induced obesity mouse model.
Figure 18A:
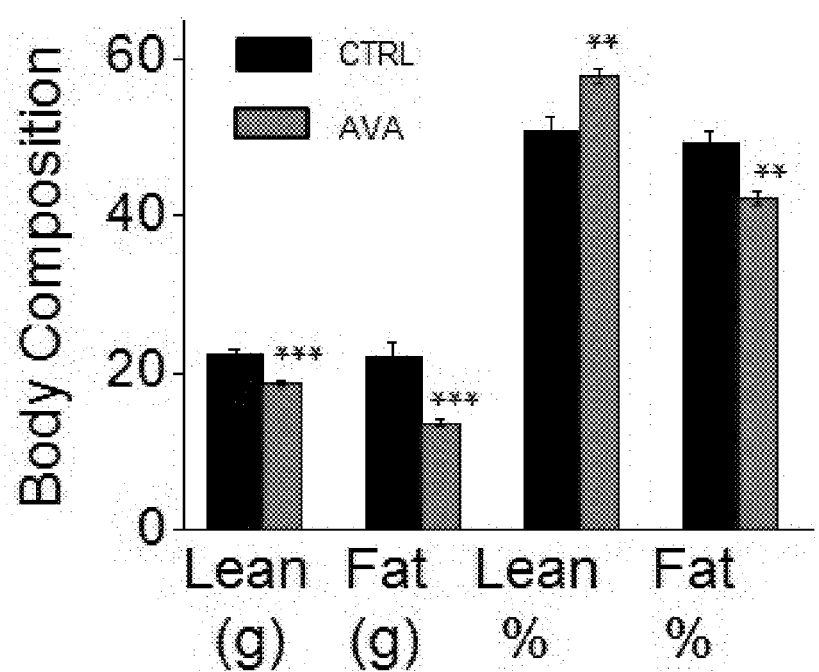
FIG. 18A is a bar graph showing the loss of whole body fat mass by avasimibe in a high-fat diet-induced obesity mouse model.
Figure 18B:
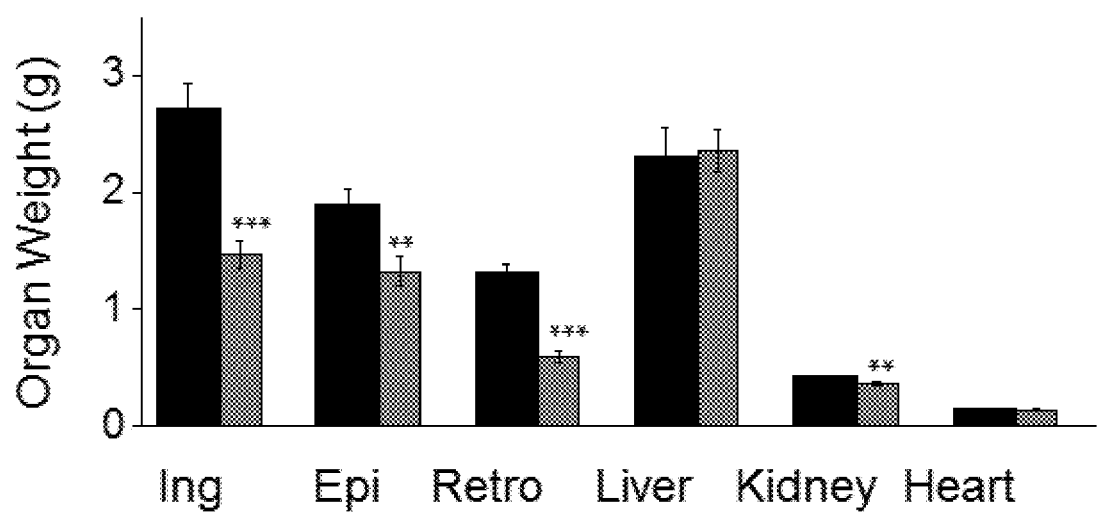
FIG. 18B is a bar graph showing the loss of white adipose tissues (Ing: inguinal, Epi: epididymal) weight by avasimibe in a high-fat diet-induced obesity mouse model, compared with non-adipose tissues.
Figure 19:
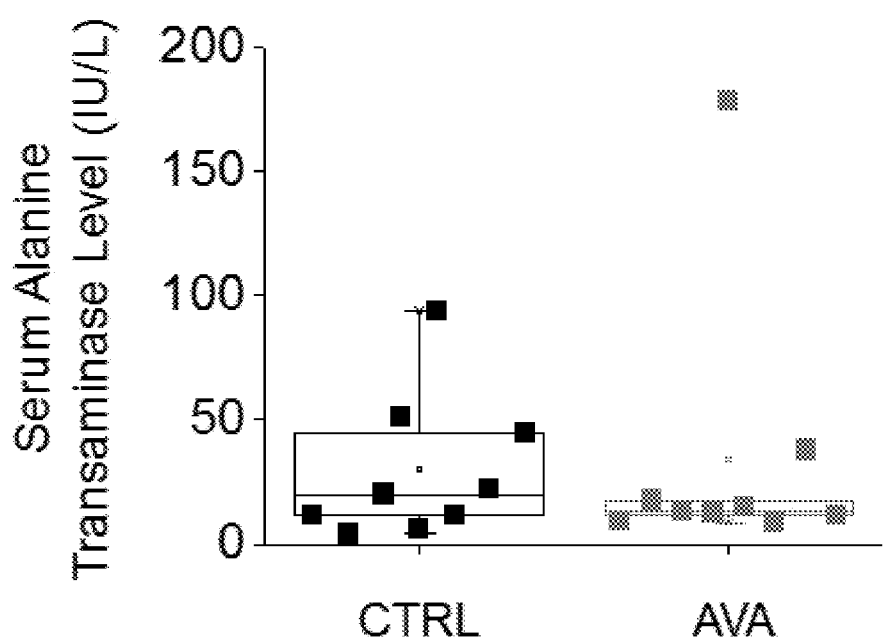
FIG. 19 is a graph representing the results of the serum alanine transaminase assay showing that avasimibe does not exhibit noticeable liver toxicity.
Figure 20A:
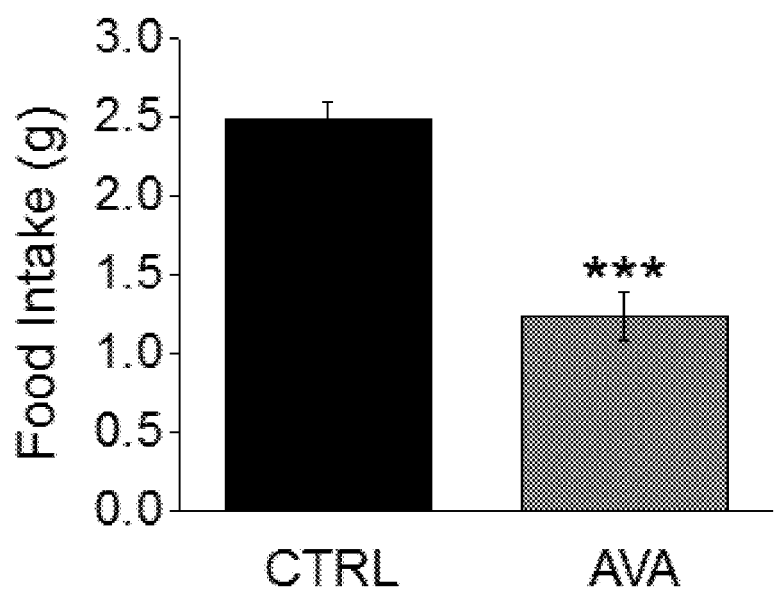
FIG. 20A is a bar graph showing the suppressed food intake by avasimibe in a high-fat diet-induced obesity mouse model.
Figure 20B:
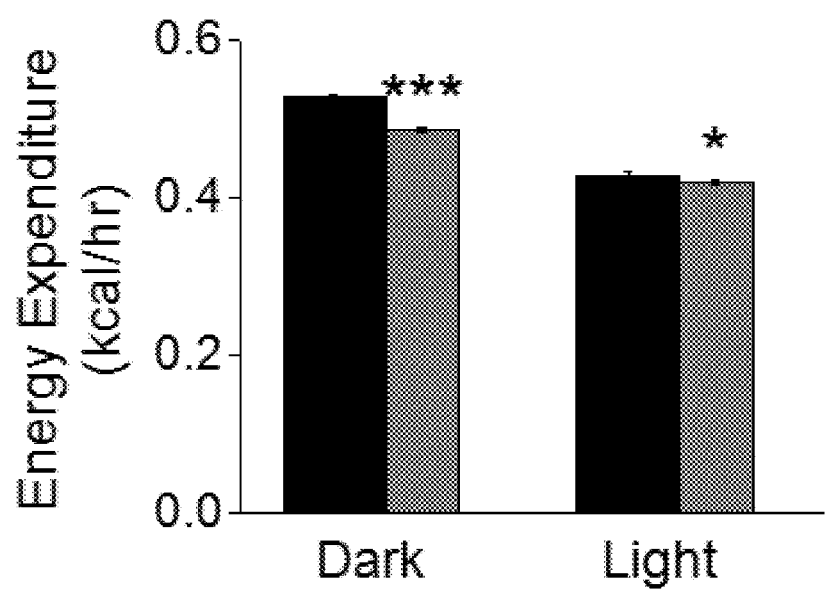
FIG. 20B and FIG. 20C are bar graphs showing the suppressed energy expenditure and the suppressed respiratory exchange ratio by avasimibe in a high-fat diet-induced obesity mouse model, encompassing the dark and the light phases.
Figure 20C:
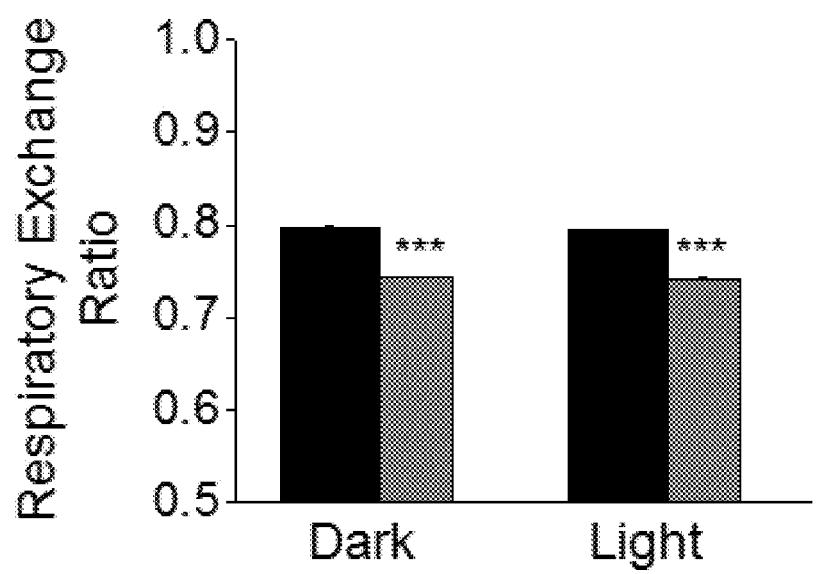
Figure 21A:
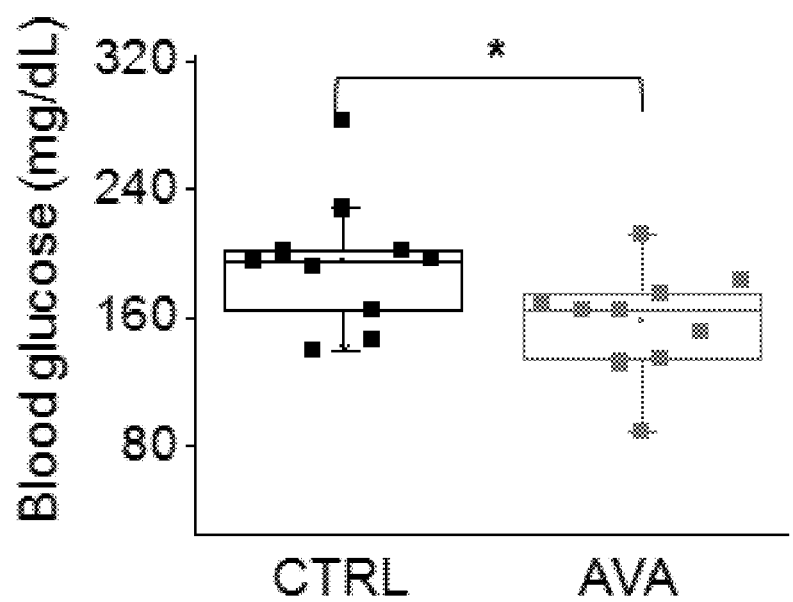
FIG. 21A and FIG. 21B are graphs showing the suppressed blood glucose levels and the suppressed insulin levels by avasimibe in a high-fat diet-induced obesity mouse model.
Figure 21B:
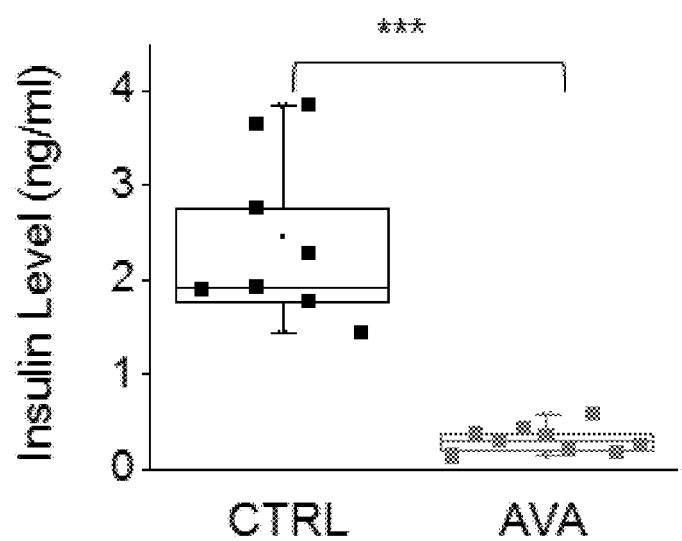
Figure 21C:
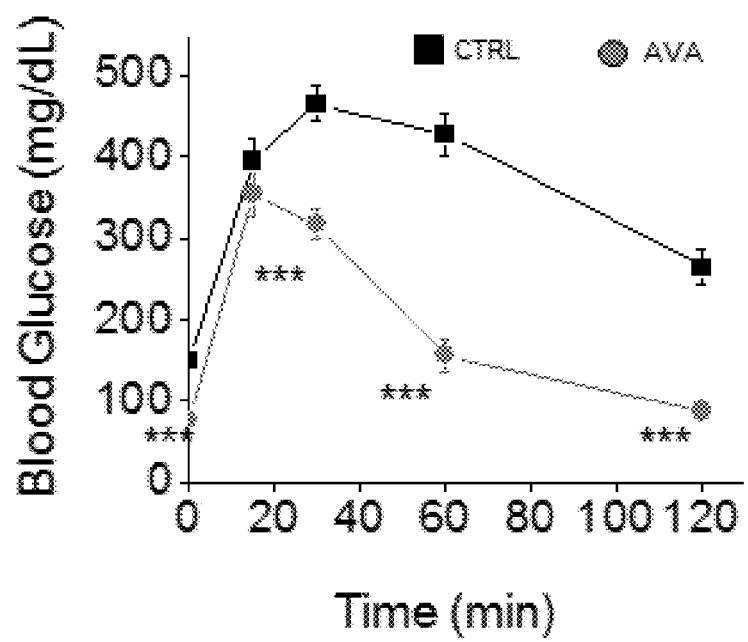
FIG. 21C is a graph showing the improved glucose tolerance by avasimibe in a high-fat diet-induced obesity mouse model.
Figure 21D:
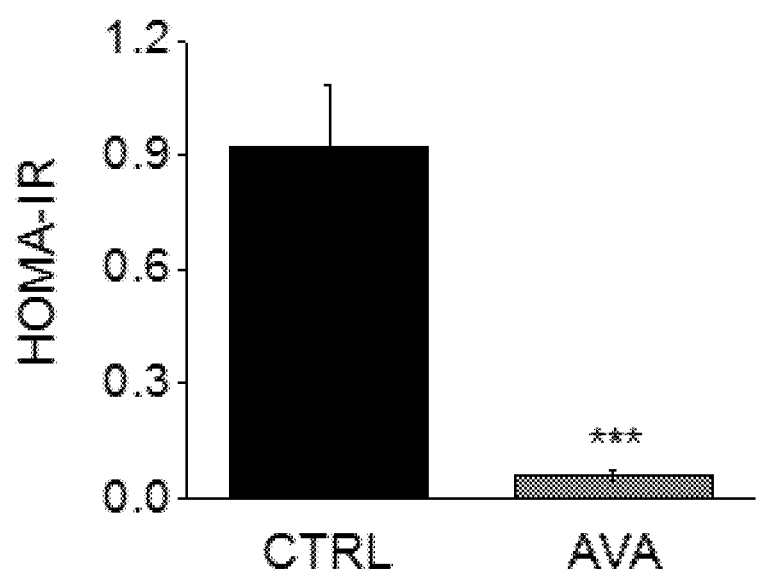
FIG. 21D is a bar graph showing the improved homeostatic model assessment of insulin resistance (HOMA-IR) value by avasimibe in a high-fat diet-induced obesity mouse model.

Example 6: Anti-Diabetic Effect of Avasimibe in Mice with High-Fat Diet-Induced Obesity an Insulin Resistance Tissue- and isoform-specific regulation of ACATs has been proposed to be therapeutic strategy for cholesterol dysregulated diseases, such as atherosclerosis. However, the therapeutic role of ACATs in obesity has never been explored. Using high fat diet-fed C57BL/6J obese and diabetic mice, a daily i.p. injection of avasimibe (20 mg/kg body weight) for about 2-week resulted in about 25% reduction or suppression in total body weight gain (FIG. 17A and FIG. 17B) along with a significant loss of whole body fat mass (FIG. 18A) and white adipose tissue (Ing: inguinal adipose tissue, Epi: epididymal adipose tissue, Retro: retroperitoneal adipose tissue) weight (FIG. 18B) with no noticeable liver toxicity as judged by alanine transaminase (ALT) assay (FIG. 19). Avasimibe treatment resulted in approximately 50% decrease in food intake (FIG. 20A). This in turn reduced energy expenditure (FIG. 20B) with a shift of energy utilization pattern of tested mice from dietary carbohydrates to lipids stored in adipose tissue, as demonstrated by reduced respiratory exchange ratio in avasimibe-treated mice and blood glucose levels (FIG. 20C) compared with control mice. Moreover, a 2-week of avasimibe administration to obese and diabetic mice resulted in marked reduction of blood glucose (FIG. 21A) and insulin levels (FIG. 21B), improved glucose tolerance (FIG. 21C) and homeostatic model assessment of insulin resistance (HOMA-IR) values (FIG. 21D).

Figure 22A:
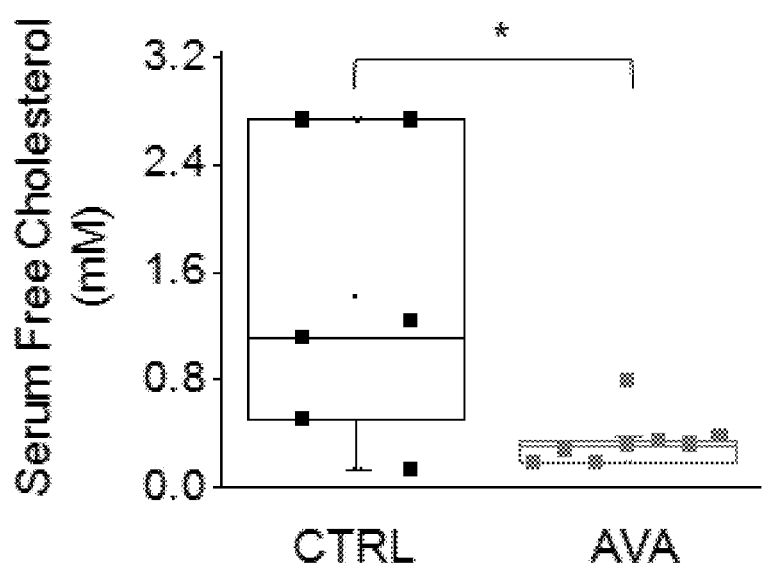
FIG. 22A, FIG. 22B and FIG. 22C are graphs showing the suppressed serum free cholesterol level, the suppressed serum cholesteryl ester level and the suppressed serum triglyceride (TG) level by avasimibe in a high-fat diet-induced obesity mouse model.
Figure 22B:
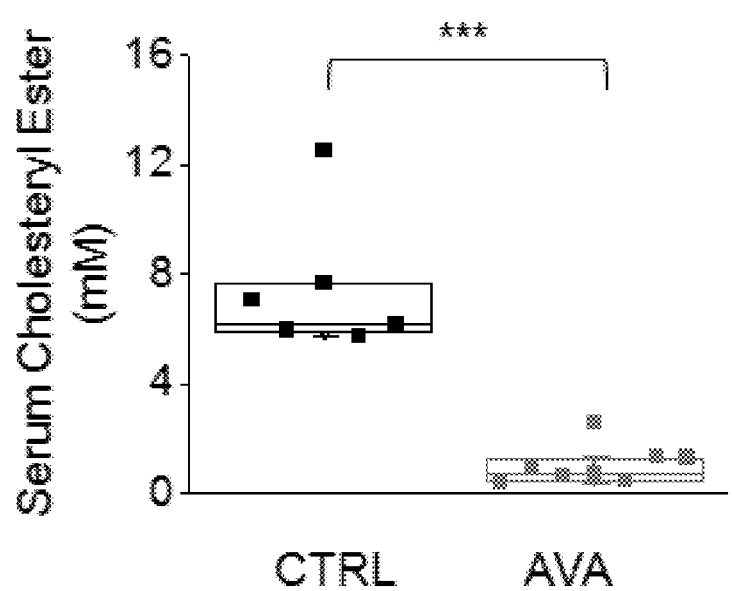
Figure 22C:
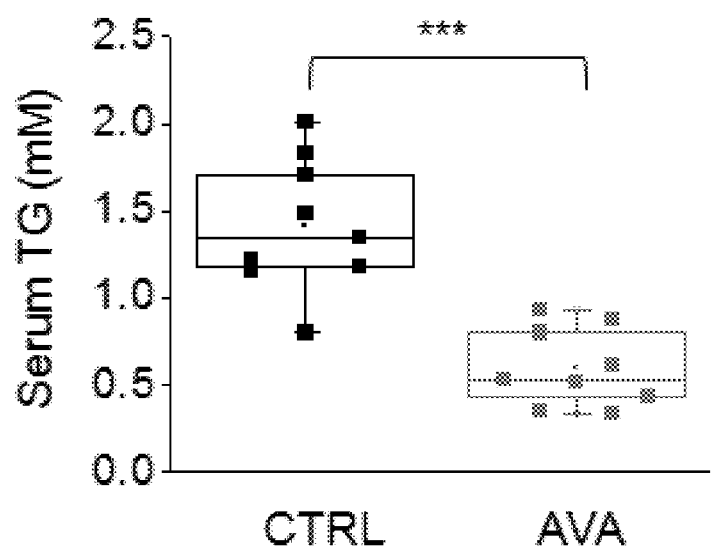
Figure 22D:
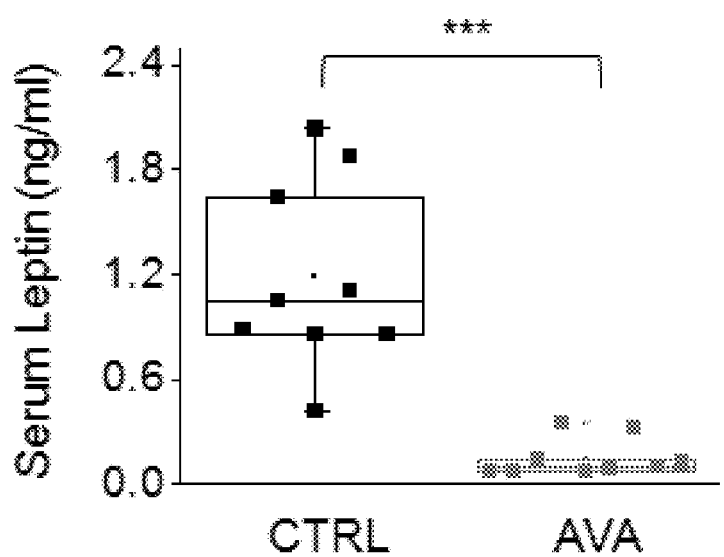
FIG. 22D is a graph showing the suppressed serum leptin level by avasimibe in a high-fat diet-induced obesity mouse model.

Avasimibe-treated mice exhibited significantly improved blood lipid profile such as a decrease in free cholesterol (FIG. 22A), CE (FIG. 22B), and TG (FIG. 22C). Consistent with reduced or suppressed adipose tissue mass shown in FIG. 18A and FIG. 18B, circulating leptin level, an adipose tissue-secreted satiety hormone that regulates whole body energy balance by inhibiting food intake behavior, was markedly suppressed by avasimibe treatment (FIG. 22D).

Figure 23A:
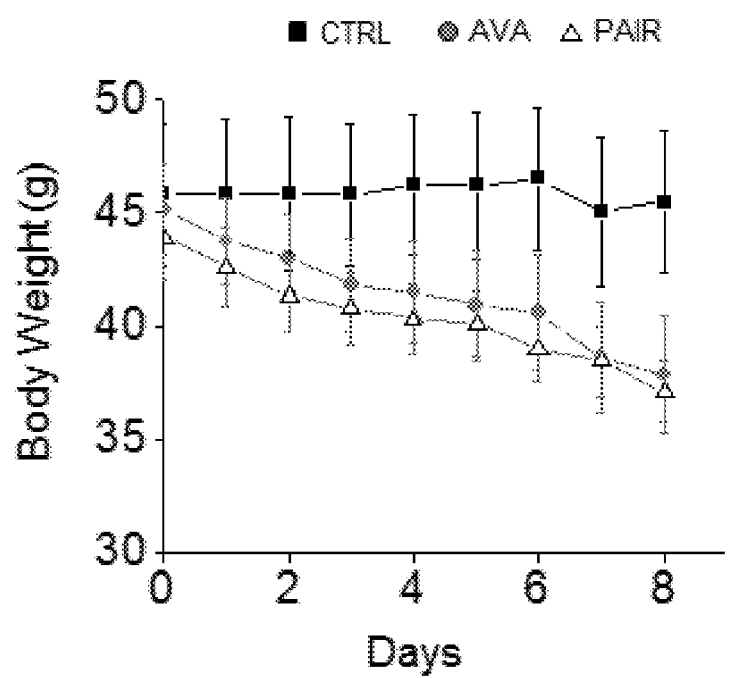
FIG. 23A is a graph showing the progressive loss of body weight by avasimibe and by pair-feeding in a high-fat diet-induced obesity mouse model.
Figure 23B:
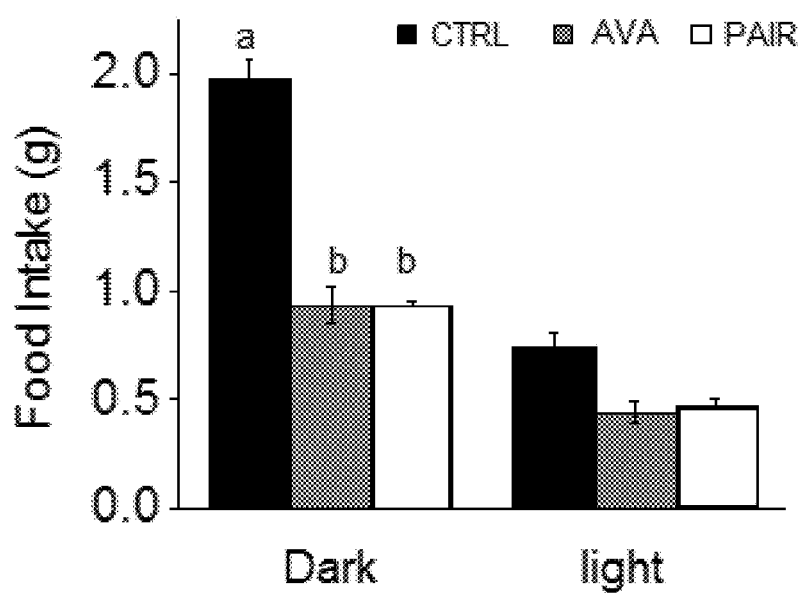
FIG. 23B, FIG. 23C and FIG. 23D are bar graphs showing the suppressed food intake, the suppressed fecal excretion and the suppressed fecal energy excretion by avasimibe and by pair-feeding in a high-fat diet-induced obesity mouse model.
Figure 23C:
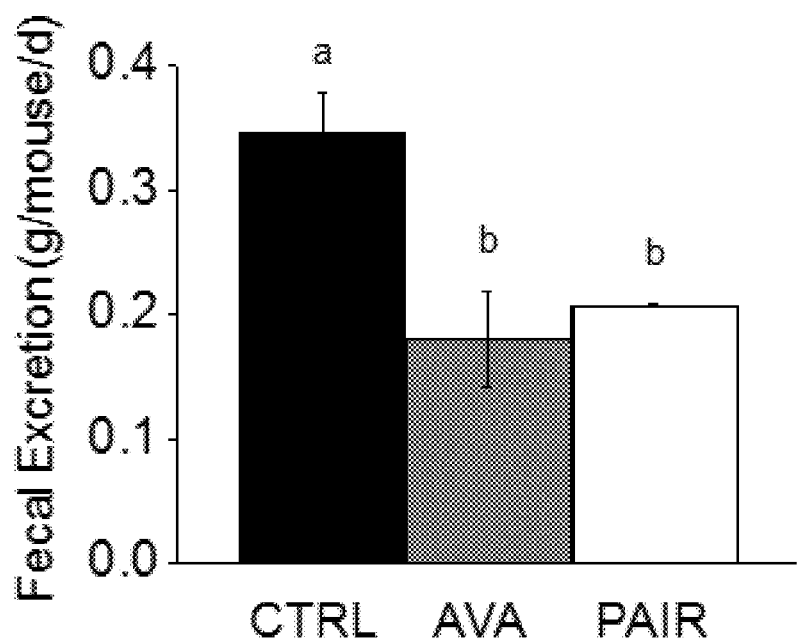
Figure 23D:
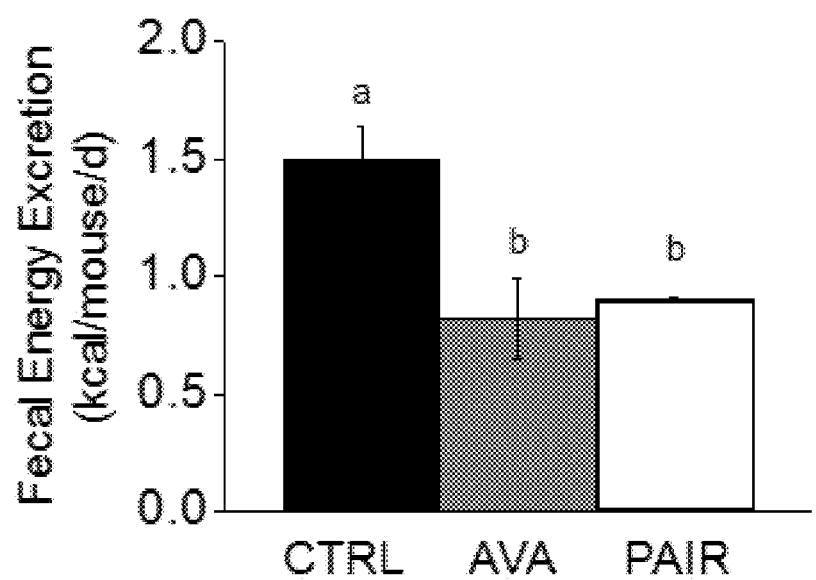

Since ACAT1 inhibitor resulted in a dramatic decrease in food intake, the reason for avasimibe's action to decrease or suppress food intake was tested for its efficacy on lowering obesity phenotypes and insulin resistance. To do this, mice were pair-fed with the amount of food consumed by avasimibe-administrated mice for 8 days. Both avasimibe-treated mice and pair-fed mice showed similar levels of body weight loss (FIG. 23A) and food intake (FIG. 23B) with little change in the fecal energy content (FIG. 23C and FIG. 23D).

Figure 23E:
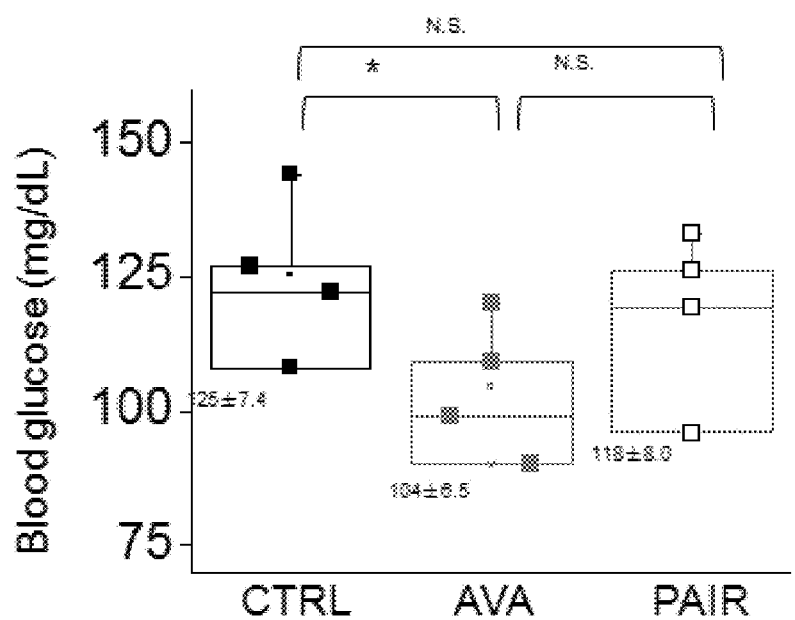
FIG. 23E is a graph showing that pair-feeding suppresses the blood glucose level in a high-fat diet-induced obesity mouse model, but not as effectively as avasimibe does.

Interestingly, mice in pair-fed group showed lower blood glucose level compared with the control group but didn't reach to the level found from avasimibe-treated mice (FIG. 23E). Thus, these results provided evidence that inhibition of ACAT1 activity in a diet-induced obese and diabetic mice are a useful strategy for treating T2D with a benefit of body weight loss.

Here, ACAT inhibitors, avasimibe and CI-976, have been identified as a highly effective anti-diabetes treatment. It is anticipated that the method of the present invention could involve administration of an ACAT1 inhibitor either alone or in combination with other drugs by any desired route known to have efficacy in treating symptoms of T2D and obesity.

Those skilled in the art will recognize that numerous modifications can be made to the specific implementations described above. The implementations should not be limited to the particular limitations described. Other implementations may be possible.

Example 7: Proteomic Analysis of Proteins Influenced by Avasimibe in Adipocytes Using LC MS/MS In order to get a comprehensive view about the role of ACAT in the LD development during adipogenesis and explore new molecular targets influenced by ACAT inhibition, we employed a global proteomic approach to investigate the effect of ACAT inhibition on adipocyte proteomes in a 3T3-L1 preadipocyte model.

Material and Methods

1. Cell Preparation and Digestion

3T3-L1 preadipocytes were induced to differentiate into mature adipocytes with the same culture condition as described elsewhere. The cells were treated with avasimibe (10 µM) or DMSO during day 2 to 6, which is the period when LD forms. Avasimibe or DMSO was replaced freshly every 48 h. Each condition was cultured in triplicate. On day 6, adipocytes were washed with 1× PBS and scraped off the culture dishes. Adipocyte cell pellets were collected after centrifugation and subsequently digested with trypsin (Sigma-Aldrich, St. Louis MO, USA) at the ratio of 1:50 (µg/µg) trypsin to protein.

2. LC MS/MS and Proteomic Analysis

The tryptic peptides after trypsin digestion were separated on a nano LC system (1100 Series LC. Agilent Technologies, Santa Clara, CA) as described previously (D'Aquila, et al. 2015). Briefly, peptides were concentrated with Agilent 300SB-C18 enrichment column and separated with C18 reversed phase ZORBAX 300SB-C18 column. High resolution hybrid ion trap mass spectrometer LTQ-Orbitrap LX (Thermo Fisher Scientific, Waltham MA, USA) was employed to identify the peptides in the data-dependent positive acquisition mode. These experiments were done in Bindley Bioscience Center. We used the MaxQuant computational proteomics platform version 1.5.3.17 (Cox and Mann, 2008) to analyze the results from LC MS/MS analysis. The *Mus musculus* (24754 entries) sequence from UNIPROT retrieved on Sep. 1, 2015 and a common contaminants database were used as our reference databases. MaxQuant was set with parameters as follows: minimum peptides length was set to seven amino acids, and "Match between runs" interval was set to one minute; The FASTA databases were randomized and 1% of protein false discovery rate was allowed; With trypsin digestion, two missed cleavages were accepted; Three modifications per peptide were allowed, including one fixed modification as "Iodo-ethanol" and variable modifications as "Oxidation (M)" and "Acetyl (Protein N-term)"; Initial precursor was set to 0.07 and fragment mass tolerance set to 0.02 Da; Data were analyzed with "Label-free quantification" (LFQ) checked.

The MaxQuant results were used in in-house script to remove all the common contaminant proteins and to calculate the average LFQ intensity values for the biological replicates and log transform [log 2 (x)]. The missing values were left blank unless indicated. A two tailed student t-test was performed on the LFQ intensity.

Results and Discussion

1. Proteins Identified Through LC MS/MS

Figure 24:
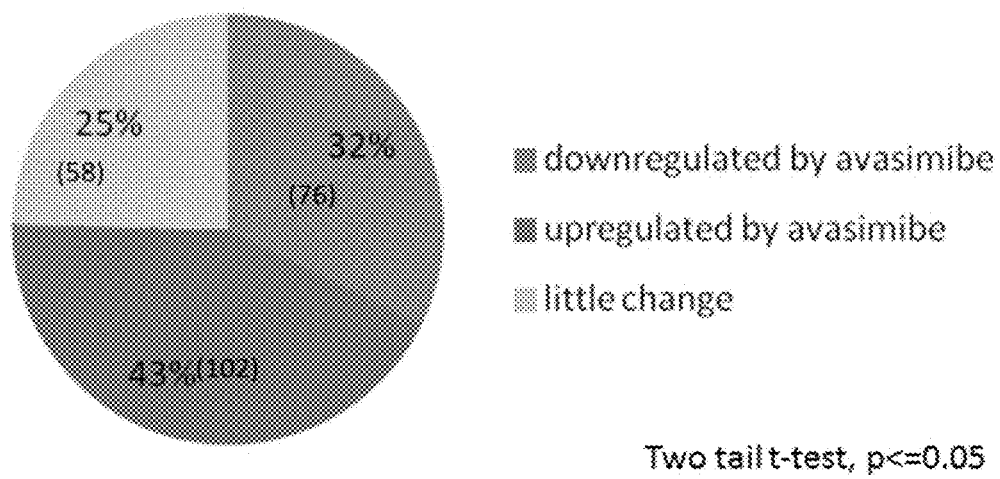
FIG. 24 is a pie chart showing the number of proteins influenced by avasimibe in adipocytes identified through LC MS/MS.

The proteomes of 3T3-L1 adipocytes (D6) cultured with or without avasimibe (10 µM) (n=3) during the LD formation stage (i.e., Day 2-Day 6) were analyzed. 669 proteins were detected and identified. The analysis was limited to proteins which were identified in all three biological replicates (217+10+9=236 proteins). Further analysis (FIG. 24) revealed that ACAT inhibition decreased or suppressed the levels of 76 identified proteins, increased the levels of 102 identified proteins, and did not alter the levels of 58 proteins significantly.

When the data were filtered with the criteria that an abundance change of ≥2-fold increase or decrease (log 2 T−log 2 C>1 or <−1, and empty values were filled with half of the lowest intensity value, i.e., 6.3462−1=5.3462), it was found that avasimibe treatment increased the levels of 22 proteins and decreased the levels of 53 proteins. These 75 proteins were further analyzed by the Database for Annotation, Visualization and Integrated Discovery (DAVID) protein analysis, and the results listed in FIG. 25-FIG. 27 are described below.

2. Proteomic Result is Consistent with the Previous Finding In Vitro.

This proteomics analysis found that 7 identified proteins associated with FA metabolic process were downregulated with avasimibe treatment. These 7 proteins were categorized into 2 groups: 1) lipogenesis related proteins: Acyl-CoA synthetase long-chain family member 1 (86% reduction), FAS (only identified in the control group); 2) mitochondrial FA β-oxidation related proteins: Acyl-CoA dehydrogenase (56% reduction), enoyl CoA hydratase short chain 1 (64% reduction), hydroxyacyl-CoA dehydrogenase (64% reduction), acetyl-CoA acyltransferase 1 (61% reduction), carnitine O-acetyltransferase (only identified in the control group) and hydroxysteroid (17-β) dehydrogenase 4 (38% reduction).

Additionally, it was found that ACAT inhibition also downregulated the protein levels of adipocyte markers, including adiponectin (84% reduction) and fatty acid binding protein 4 (64% reduction). There were 3 identified proteins associated with cholesterol metabolism. Among them, cytochrome B5 Reductase 3 (involved in cholesterol biosynthesis) and superoxide dismutase 1 (associated with negative regulation of cholesterol biosynthesis) were not altered significantly by ACAT inhibition, while sterol carrier protein 2 (for bile acid biosynthesis) was downregulated by 36%. Considering de novo cholesterol synthesis is limited in adipocytes, it was speculated that ACAT inhibition may not alter cholesterol biosynthesis significantly, although enzyme activity assay is needed to confirm it.

Notably, avasimibe is known to inhibit cytochrome P450 (CYP450), the major drug metabolizing enzymes (Sahi, et al. 2004). Similarly, the current proteomics result suggested that ACAT inhibition reduced or suppressed the protein level of cytochrome B5 Type A (67% reduction), which is involved in CYP450 pathway. Taken together, the proteome analysis support that ACAT inhibition downregulated proteins involved in lipogenesis and delayed adipogenesis in vitro.

3. Cytoskeleton May be Involved in the Suppression of LD Development by ACAT Inhibition.

During adipogenesis, cell morphology changes from flat to spherical, and this morphological change is explained by cytoskeletal remodeling, including fragmentation of microtubules and depolymerization of actin microfilaments during adipogenesis (Smas and Sul 1995; Welsh, et al. 2004). Moreover, it is well known that almost all the detected cytoskeletal protein levels decrease during adipogenesis (Soukas, et al. 2001; Welsh, et al. 2004). The Database for Annotation, Visualization and Integrated Discovery (DAVID) analysis of the aforementioned proteomics study revealed that the proteins upregulated by avasimibe were primarily associated with cytoskeletons. This could explain how ACAT inhibition delayed adipogenesis process. It is known that cytoskeleton proteins are required for stabilizing the newly generated LDs in human adipocytes (Heid, et al. 2014). However, it is unclear whether avasimibe suppressed LD development through cytoskeleton remodeling or not. These results propose a hypothesis whether ACATs affect LD development via cytoskeleton remodeling.

The invention claimed is:

1. A method for controlling abnormally increased appetite for consumption of food, the method comprising parenterally administering at least once in a month to an obese subject with Prader-Willi syndrome (PWS) a composition comprising an effective amount of avasimibe or a pharmacologically acceptable salt thereof that non-selectively inhibits in vivo both acyl-coenzyme A:cholesterol acyltransferase 1 (ACAT1) and acyl-coenzyme A:cholesterol acyltransferase 2 (ACAT2),
wherein the degree that the avasimibe or the pharmacologically acceptable salt thereof inhibits ACAT1 is less than the degree that the avasimibe inhibits ACAT2.

2. The method of claim 1, wherein the effective amount is in the range of about 0.01 mg/kg/day to about 200 mg/kg/day.

3. The method of claim 1, wherein the composition is administered subcutaneously, intravenously, intraperitoneally, intranasally, or intracerebrally.

4. The method of claim 1, wherein the active agent improves a diabetic condition of the obese PWS subject.

5. The method of claim 1, wherein the active agent reduces a body weight of the obese PWS subject.

6. The method of claim 1, wherein the obese PWS subject administered with the composition has a decreased level of free cholesterol, cholesterol ester (CE), triglyceride (TG), or any combination thereof compared to an obese PWS subject having high fat diet without the administration of the composition.

7. The method of claim 1, wherein the composition is formulated in the form of a microsphere, a microcapsule, a nanoparticle, or a liposome in which the active agent contained.

8. The method of claim 1, wherein the composition is formulated in the form of an applicator stick, a lotion, a cream, an ointment, a gel, a jelly, a paint, a powder, an aerosol, a foam, a patch, a suspension, or a solution in which the active agent is contained.

9. The method of claim 1, wherein the composition further comprises at least one additional active agent.

10. The method of claim 9, wherein the additional agent is another ACAT inhibitor.

11. The method of claim 9, wherein the additional agent is an anti-diabetes drug.

12. The method of claim 9, wherein the additional agent is a glucagon-like peptide-1 receptor agonist.

13. The method of claim 12, wherein the glucagon-like peptide-1 receptor agonist is selected from the group consisting of exenatide, liraglutide, and albiglutide.

14. The method of claim 9, wherein the additional active agent is an anti-obesity drug.

15. The method of claim 9, wherein the additional agent is selected from the group consisting of Sibutramine, Phentermine, Mazindol, Diethylpropion, Leptin, Orlistat, a Beta-3 agonist, and Rimonabant.

16. The method of claim 1, wherein the composition is co-administered with an additional composition comprising an additional active agent simultaneously or separately.

17. The method of claim 1, wherein the composition is administered at least once in a week.

18. The method of claim 1, wherein the composition is administered at least once in a day.

* * * * *

SEQUENCE LISTING

```
Sequence total quantity: 6
SEQ ID NO: 1            moltype = AA  length = 162
FEATURE                 Location/Qualifiers
source                  1..162
                        mol_type = protein
                        organism = Homo sapiens
SEQUENCE: 1
MAVLPALLRS GARSRSPLLR RLVQEIRYVE RSYVSKPTLK EVVIVSATRT PIGSFLGSLS   60
LLPATKLGSI AIQGAIEKAG IPKEEVKEAY MGNVLQGGEG QAPTRQAVLG AGLPISTPCT  120
TINKVCASGM KAIMMASQSL MCGHQIKQET GSLAKICCHV RR                    162

SEQ ID NO: 2            moltype = DNA  length = 1370
FEATURE                 Location/Qualifiers
source                  1..1370
                        mol_type = genomic DNA
                        organism = Homo sapiens
SEQUENCE: 2
ggggagtcta cgcctgtgga gccgatactc agcccactgc gaccatggct gtgctgccgg   60
cacttctgcg cagcggcgcc cgcagccgca gcccctgct ccggaggctg gtgcaggaaa  120
taagatatgt ggaacggagt tatgtatcaa aacccacttt gaaggaagtg gtcatagtaa  180
gtgctacaag aacacccatt ggatcttttt taggcagcct ttccttgctg ccagccacta  240
agcttggttc cattgcaatt cagggagcca ttgaaaaggc agggattcca aaagaagaag  300
tgaaagaagc atacatgggt aatgttctac aaggaggtga aggacaagct cctacaaggc  360
aggcagtatt gggtgcaggc ttacctattt ctactccatg taccaccata aacaaagttt  420
gtgcttcagg aatgaaagcc atcatgatgg cctctcaaag tcttatgtgt ggacatcaga  480
tcaagcaaga gacaggctcc ttagcaaaaa tatgctgtca tgtcaggagg tgagacctgg  540
acacacagaa gaatcaagat tctctcagat ctgagccctt cattttcag atgaagattt  600
ttttcagtg tgtctgagac agccacagag ttacagggct gagcatctgc catgtgacag  660
tcattggaaa tagagtggtg aacaaaacat ttaaaaaaat ctgtacatgt gcaggtctct  720
gttggaaaaa tgcctaaaag aaatgctgag tcaggatttg aacattttgg tatttgcaaa  780
tgctttccat aaaagttgta ccagttagac tttccaaaaa ttgtgtgact tgtctggatc  840
tgcaccacca ctgggtggta ccaaaccctt gtcaaactgg taggtgaaaa acggtcacca  900
gatttagttt cagaactgtt tgtcatggaa agttttgtct taattgaagt attgtggttc  960
tctagcaaat gccatttgta ctatattgaa atactttcat ttaatattat tttattcatt 1020
```

-continued

```
tgtggatata  tacagtgact  tataggcatt  cttggaagtg  ctttgttttg  aatatttatg   1080
accttagaaa  acagtcagtt  ttactttata  atgaagaatt  gataccttat  tttctgtcac   1140
ttattattgc  catcaccccc  agtaaaaagt  acaagtgaat  aaaacttaga  tgagaactga   1200
ttaagaattt  ctctatttcg  gaataggcaa  aatatttatg  tttctttggt  atagagcttg   1260
cttgtctgta  tgcctgatta  aagactgtaa  gaagatatta  ttggctttat  gtttacatta   1320
atgttttata  ttaaactgtt  tttaactagc  gaaaaaaaaa  aaaaaaaaa                1370

SEQ ID NO: 3           moltype = AA   length = 397
FEATURE                Location/Qualifiers
source                 1..397
                       mol_type = protein
                       organism = Homo sapiens
SEQUENCE: 3
MNAGSDPVVI VSAARTIIGS FNGALAAVPV QDLGSTVIKE VLKRATVAPE DVSEVIFGHV    60
LAAGCGQNPV RQASVGAGIP YSVPAWSCQM ICGSGLKAVC LAVQSIGIGD SSIVVAGGME   120
NMSKAPHLAY LRTGVKIGEM PLTDSILCDG LTDAFHNCHM GITAENVAKK WQVSREDQDK   180
VAVLSQNRTE NAQKAGHFDK EIVPVLVSTR RGLIEVKTDE FPRHGSNIEA MSKLKPYFLT   240
DGTGTVTPAN ASGINDGAAA VVLMKKSEAD KRGLTPLARI VSWSQVGVEP SIMGIGPIPA   300
IKQAVTKAGW SLEDVDIFEI NEAFAAVSAA IVKELGLNPE KVNIEGGAIA LGHPLGASGC   360
RILVTLLHTL ERMGRSRGVA ALCIGGGMGI AMCVQRE                            397

SEQ ID NO: 4           moltype = DNA   length = 1443
FEATURE                Location/Qualifiers
source                 1..1443
                       mol_type = genomic DNA
                       organism = Homo sapiens
SEQUENCE: 4
ggagaagcaa  gatgaatgca  ggctcagatc  ctgtggtcat  cgtctcggcg  gcgcggacca    60
tcataggttc  cttcaatggt  gccttagctg  ctgttcctgt  ccaggacctg  ggctccactg   120
tcatcaaaga  agtcttgaag  agggccactg  tggctcccga  agatgtgtct  gaggtcatct   180
ttggacatgt  cttggcagca  ggctgtgggc  agaatcctgt  tagacaagcc  agtgtgggtg   240
caggaattcc  ctactctgtt  ccagcatgga  gctgccagat  gatctgtggg  tcaggcctaa   300
aagctgtgtg  ccttgcagtc  cagtcaatag  ggataggaga  ctccagcatt  gtggttgcag   360
gaggcatgga  aaatatgagc  aaggctcctc  acttggctta  cttgagaaca  ggagtaaaga   420
taggtgagat  gccactgact  gacagtatac  tctgtgatgg  tcttacagat  gcatttcaca   480
actgtcatat  gggtattaca  gctgaaaatg  tagccaaaaa  atggcaagtg  agtagagaag   540
atcaggacaa  ggttgcagtt  ctgtcccaga  acaggacaga  gaatgcacag  aaagctggcc   600
attttgacaa  agagattgta  ccagttttgg  tgtcaactag  aagaggtctt  attgaagtta   660
aaacagatga  gtttcctcgc  catgggagca  acatagaagc  catgtccaag  ctaaagcctt   720
actttcttac  tgatggaacg  ggaacagtca  ccccagccaa  tgcttcagga  ataaatgatg   780
gtgctgcagc  tgtcgttctt  atgaagaagt  cagaagctga  taaacgtgga  cttacacctt   840
tagcacggat  agtttcctgg  tcccaagtgg  gtgtggagcc  ttccattatg  ggaataggac   900
caattccagc  cataaagcaa  gctgttacaa  aagcaggttg  gtcactggaa  gatgttgaca   960
tatttgaaat  caatgaagcc  tttgcagctg  tctctgctgc  aatagttaaa  gaacttggat  1020
taaacccaga  gaaggtcaat  attgaaggag  gggctatagc  cttgggccac  cctcttggag  1080
catctggctg  tcgaattctt  gtgaccctgt  tacacacact  ggagagaatg  ggcagaagtc  1140
gtggtgttgc  agccctgtgc  attggggtg   ggatgggaat  agcaatgtgt  gttcagagag  1200
aatgaattgc  ttaaactttg  aacaacctca  atttctttt   aaactaataa  agtactaggt  1260
tgcaatatgt  gaaatcagag  gaccaaagta  cagatgaaaa  ccatttccta  catcacaaaa  1320
acccaagttt  acagcttgta  ctttacttta  atgtgtaata  ctcaactcaa  ggtacaagac  1380
aattgcattt  aacattgtta  taaataaaag  gaacatcaga  tcaatcaaaa  aaaaaaaaa   1440
aaa                                                                  1443

SEQ ID NO: 5           moltype = RNA   length = 59
FEATURE                Location/Qualifiers
source                 1..59
                       mol_type = genomic RNA
                       organism = Mus musculus
SEQUENCE: 5
ccggccaacc  agagactaaa  catatctcga  gatatgttta  gtctctggtt  ggttttttg     59

SEQ ID NO: 6           moltype = RNA   length = 59
FEATURE                Location/Qualifiers
source                 1..59
                       mol_type = genomic RNA
                       organism = Mus musculus
SEQUENCE: 6
ccggtgcggt  ggttcatgag  tatatctcga  gatatactca  tgaaccaccg  catttttg     59
```